US006815170B1

(12) United States Patent
Morton

(10) Patent No.: US 6,815,170 B1
(45) Date of Patent: Nov. 9, 2004

(54) METHODS FOR LYMPH NODE IDENTIFICATION

(75) Inventor: Donald L. Morton, Pacific Palisades, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 553 days.

(21) Appl. No.: 09/609,301

(22) Filed: Jun. 30, 2000

Related U.S. Application Data

(60) Provisional application No. 60/142,006, filed on Jun. 30, 1999.

(51) Int. Cl.$^7$ .......................... G01N 33/574; G01N 1/30
(52) U.S. Cl. ...................................... 435/7.23; 435/40.5
(58) Field of Search ............................... 435/7.23, 40.5

(56) References Cited

U.S. PATENT DOCUMENTS

| | | | |
|---|---|---|---|
| 5,069,662 A | | 12/1991 | Bodden .......................... 604/4 |
| 5,116,615 A | | 5/1992 | Gokcen et al. ............. 424/94.2 |
| 5,582,172 A | | 12/1996 | Papisov et al. .......... 128/653.4 |
| 5,732,704 A | * | 3/1998 | Thurston et al. ............. 600/431 |
| 5,817,012 A | | 10/1998 | Schoendorfer .............. 600/362 |
| 5,928,669 A | | 7/1999 | Davis et al. ................. 424/489 |
| 6,205,352 B1 | * | 3/2001 | Carroll ........................ 600/431 |

OTHER PUBLICATIONS

Hagiwara et al., "Lymph Nodal Vital Staining with Newer Carbon Particle Suspensions Compared with Indla Ink: Experimetntal and Clinical Observations", Lumphology 25 : 84–89 (1992).*
Albertini et al., "Lymphatic mapping and sentinel node biopsy in the patient with breast cancer," JAMA, 276:1818–1822, 1996.
Anderson et al.,. "Tattoo pigment mimicking metastatic malignant melanoma," Dermatol Surg., 22:92–94, 1996.
Bilchik et al., "Universal application of intraoperative lymphatic mapping and sentinel lymphadenectomy in solid neoplasms," Cancer J, 4:351–358, 1998.
Bostick et al., "Intraoperative lymphatic mapping for early–stage melanoma of the head and neck," Am J Surg, 174:536–539, 1997.
Botoman et al., "Localization of colonic lesions with endoscopic tattoo," Dis Colon Rectum, 37:775–776, 1994.
Brandwood et al., "Phagocytosis of carbon particles by macrophages in vitro," Biomaterials, 13:646–648, 1992.
Eriguchi et al., "Regional lymph node metastasis of early gastric cancer," Eur J Surg, 157:197–200, 1991.
Fennerty et al., "Effectiveness of India ink as a long–term colonic mucosal marker," Am J Gastroenterol, 87:79–81, 1992.
Gershenwald et al., "Patterns of recurrence following a negative sentinel lymph node biopsy in 243 patients with stage 1 or II melanoma," J. Clin Oncol, 16:2253–2260, 1998.

Giuliano et al., "Sentinel lymphadenectomy in breast cancer," J Clin Oncol, 15:2345–2350, 1997.
Giuliano et al., "Lymphatic Mapping and Sentinel Lymphadenectomy for Breast Cancer", Annals of Surgery, 220(3):391–401, 1994.
Glass et al., "Kinetics of three lymphoscintigraphic agents in patients with cutaneous melanoma," J Nucl Med, 39: 1185–1190, 1998.
Hagiwara et al., "A pilot study of fiberscopy–guided local injection of anti–cancer drugs bound to carbon particles for control of rectal cancer," ABSTRACT, Anticancer Drugs, 9(4):363–367, 1998.
Hagiwara et al., "Activated carbon particles as an anti–cancer drug carrier into regional lymph nodes," ABSTRACT, Anticancer Drug Des., 1(4):313–321, 1987.
Hagiwara et al., "Anticancer agents adsorbed by activated carbon particles, a new form of dosage enhancing efficacy on lymphnodal metastases," Anticancer Res, 6:1005–1008, 1986.
Hagiwara et al., "Local injection if anti–cancer drugs bound to carbon particles for early gastric cancer—a pilot study," ABSTRACT, Hepatogastroenterology, 47(32):575–578, 2000.
Imanishi et al., "Trial of a treatment for lymph nodes in metastases in patients with breast cancer using aclarubic in bound to activated carbon particles," ABSTRACT, Gan To Kagaku Ryoho, 22(11):1635–1637, 1995.
Kapteijn et al., "Localizing the sentinel node in cutaneous melanoma: gamma probe detection versus blue dye," Ann Surg Oncol, 4:156–160, 1997.
Kelley et al., "Lymphatic mapping and sentinel lymphadenectomy for melanoma," Semin Surg Oncol, 14:283–290, 1998.
Kitamura et al., "Activated carbon–oriented gastrectomy for early gastric cancer," Br J Surg, 82:647–650, 1995.
Kitamura et al., "Rapid and accurate method for delineating cancer lesions in laparoscopic colectomy using activated carbon injection," J Surg Oncol, 58:31–34, 1995.

(List continued on next page.)

Primary Examiner—Sandra E. Saucer
(74) Attorney, Agent, or Firm—Fulbright & Jaworski LLP

(57) ABSTRACT

The present invention describes a method for identification of lymph nodes and the presence or absence of lymph node metastases as an important prognostic factor in early stage cancers of all types. A carbon black suspension is administered in combination with a second compound to a region associated with a neoplastic tumor in a patient. The sentinel lymph node associated with the disease-associated region is identified by the accumulation of carbon particles. The region associated with the accumulation of carbon black particles is then subject to histopathology for the purpose of identification, diagnosing, staging or predicting the presence of neoplastic tissue. The neoplastic tumor is any neoplasm that metastasizes via the lymphatic channels.

51 Claims, 3 Drawing Sheets

OTHER PUBLICATIONS

Kodama and Koyama, "Indications for pylorus preserving gastrectomy for early gastric cancer located in the middle third of the stomach," *World J Surg* 15:628–634, 1991.

Kodama et al., "Study on the lymphatic flow of the lower gastric region for radical lymphadenectomy in advanced lower gastric cancer," ABSTRACT, *Nippon Geka Gakkai Zasshi*, 89(7):1008–1013, 1988.

Krag et al., "Surgical resection and radiolocalization of the sentinel node in breast cancer using gamma probe," *Surg Oncol*, 2:335–340, 1993.

Lucci et al., "Carbon dye as an adjunct to isosulfan blue for sentinel lymph node dissection," *Surgery*, 126:48–53, 1999.

Margevicius et al., "Identification and distribution of synthetic ligament wear particles in sheep," *J Biomed Mater Res*, 31:319–328, 1996.

Morton and Bostick, "Will the true sentinel node please stand?" *Ann Surg Oncol*, 6:12–14, 1999.

Morton and Chan, "Current status of intranperative lymphatic mapping and sentinel lyniphadenectotny for melanoma: is it standard of care?" *J Am Coll Surg*, 189:214–223, 1999.

Morton et al., "Intraoperative lymphatic mapping and selective cervical lymphadenectomy for early–stage melanomas of the head and neck," *J. Clin. Oncol.*, 11:1751–1756, 1993.

Morton et al., "Symposium: lymphatic mapping and sentinel node biopsy in patients with breast cancer and melanoma," *Contemp Surg*, 53:281–298 (part 1) 1998.

Morton et al., "Symposium: lymphatic mapping and sentinel node biopsy in patients with breast cancer and melanoma," *Contemp Surg*, 53:353–361 (part 2), 1998.

Morton et al., "Technical details of intraoperative lymphatic mapping for early stage melanoma," *Arch Surg*, 127:392–399, 1992.

Morton, "Intraoperative lymphatic mapping and sentinel lymphadenectomy: Community standard care or clinical investigation?" *Cancer J Sci. Am.*, 3:328–330, 1997.

Nagakawa et al., "Clinical study of lymphatic flow to the paraaortic lymph nodes in carcinoma of the head of the pancreas," *Cancer*, 73:1155–1162, 1994.

Ohyama et al., "Endoscopic injection of methotrexate bound to activated carbon particles in the treatment of gastric cancer," ABSTRACT, *Gan To Kagaku Ryoho*, 22(11) 1632–1634, 1995.

Okamoto et al., "Number and anatomical extent of lymph node metastases in gastric cancer: analysis using intralymph node injection of activated carbon particles," ABSTRACT, *Jpn. J. Clin. Oncol.*, 29(2)74–77, 1999.

Ponsky and King, "Endoscopic marking of colonic lesions," *Gastrointestinal Endoscopy* 22:42–43, 1975.

Sawai et al., "Rationale of lymph node dissection for breast cancer from the viewpoint of analysis of axillary lymphatic flow using activated carbon particle CH40," ABSTRACT, *Gan To Kagaku Ryoho*, 23 Suppl 1:30–35, 1996.

Sawai et al., "Rationalization of lymph node dissection for gastric cancer using small sized activated carbon particles absorbing absolute ethanol," ABSTRACT, *Nippon Geka Gakkai Zasshi*, 90(9):1310–1313, 1989.

Strom et al., "Retention and clearance of inhaled submicron black particles," *J Toxicol Environ Health*, 26:183–202, 1989.

Takahashi et al., "Studies on para–aortic metastatic lymph nodes in gastric cancer after endoscopic injection of activated carbon particles," ABSTRACT, *Nippon Geka Gakkai Zasshi*, 88(1):35–40, 1987.

Takahashi et al., "Type–oriented therapy for gastric cancer effective for lymph node metastasis: management of lymph node metastasis using carbon particles adsorbing an anticancer agent," *Semin Surg Oncol*, 7:378–383, 1991.

van der Veen et al., "Gamma probe–guided sentinel node biopsy to select patients with melanoma for lymphadenectomy," *Br J Surg*, 81:1769–1770, 1994.

Veronesi et al., "Sentinel–node biopsy to avoid axillary dissection in breast cancer with clinically negative lymphnodes," *Lancet*, 349:1864–1867, 1997.

Wong et al., "Lymphatic drainage of skin to a sentinel lymph node in a feline model," *Ann Surg*, 214:637–641, 1991.

Yokota et al., "Lymph–node staining with activated carbon CH40: a new method for axillary lymph–node dissection in breast cancer," *Can J Surg*, 43:191–196, 2000.

Yoshida et al., "Studies on gastric lymphatics by using activated carbon particle (CH44) and lymph node metastasis of gastric cancer," ABSTRACT, *Nippon Geka Gakkai Zasshi*, 89(5):664–670, 1988.

\* cited by examiner

METHODS FOR LYMPH NODE IDENTIFICATION

The present application claims the benefit of U.S. Provisional Patent Application Ser. No. 60/142,006, filed Jul. 1, 1999, the entire text of which is specifically incorporated by reference herein without disclaimer.

The government owns rights in the present invention pursuant to grant number CA29605 from the National Institutes of Health.

BACKGROUND OF THE INVENTION

1. Field of the Invention

The present invention relates generally to the fields of surgery, cancer and histopathology. More particularly, it concerns a method for identification of lymph nodes and the presence or absence of lymph node metastases as an important prognostic factor in early stage cancers of all types. In particular aspects, the present invention relates to carbon particle dye compositions for sentinel lymph node identification in cancers such as melanoma. In other aspects, the present invention relates to carbon particle dye compositions for use in determining the histopathologic status of sentinel lymph nodes.

2. Description of Related Art

Routine lymphadenectomy for patients with clinical stage I melanoma remains controversial. Since the first description of a technique for intraoperative lymphatic mapping and sentinel lymphadenectomy (LM/SL) (Morton et al., 1990; Morton et al., 1992), the histologic status of the sentinel node has become a widely accepted criterion upon which to base a decision for complete lymph node dissection in melanoma (Morton, 1997; Thompson et al., 1995).

A large number of studies using the mature technique of LM/SL to identify sentinel nodes with blue dye and radiocolloid support the concept that the histopathologic status of the sentinel nodes is representative of the histopathologic status of all the lymph nodes present in the same basin (Morton et al., 1993; Reintgen et al., 1994; Thompson et al., 1995; Krag et al., 1995; Pijpers et al., 1995; Albertini et al., 1996; Joseph et al., 1997; Bostick et al., 1999; Leong et al., 1997; Loggie et al., 1997; Lingam et al., 1997; Thompson et al., 1997; van der Veen et al., 1994). Unfortunately, a low but definite recurrence risk exists in the same basin after LM/SL is performed as the solitary procedure for tumor-free sentinel nodes (Essner et al., 1999; Gershenwald et al., 1998; Miliotes et al., 1996).

Recurrence in the operated basin that may be due to three reasons. First, in-transit lymphatic metastasis in evolution at the time of LM/SL may subsequently seed the basin. Unfortunately, surgeons presently have no control over this biologic phenomenon.

Second, LM/SL is fallible because a false-negative rate exists due to a failure of surgery, lymphoscintigraphy or histopathology (Morton and Chan, 1999; Morton and Bostick, 1999). Isosulfan Blue and Patent Blue V dyes are the most commonly used agents to identify the sentinel lymph node(s). Surgeons experienced in sentinel node mapping for melanoma have reported successful identification of the sentinel node using blue dye alone in up to 96% of cases (Morton et al., 1992; Morton et al., 1993; Kelley et al., 1998), and the technique is being applied to breast cancer and other solid neoplasms (Giuliano et al., 1997; Morton et al., 1998; Bilchik et al., 1998).

However, isosulfan blue dye-directed mapping is subject to error. The relatively rapid washout of dye from the sentinel node to successive nodes in the basin can lead to intraoperative misidentification of the sentinel node (Bostick et al., 1997; Bostick et al., 1999). This problem led to the use of radionucleotide tracers to assist in identification of the sentinel node. The tracer, usually a technetium-labeled sulfur or albumin colloid, passes through lymphatics into lymph nodes. The sentinel or "hot" node is then identified by use of a gamma counter. Unfortunately, there is still no clear definition of a sentinel node when using radionucleotide tracer technology (Morton et al., 1998). In patients with breast cancer, Krag et al. (1993) defined a sentinel node as having greater than 25 counts per 10 seconds. Veronesi et al. (1997) defined a sentinel node as having between 10 and 2000 counts per second. Others have defined the sentinel node as a lymph node having ten times as many counts as an adjacent, nonsentinel node (Albertini et al., 1996). As should be evident, these arbitrary standards can lead to confusion and misjudgement.

All blue nodes and/or all radioactive sentinel nodes may not be removed at LM/SL. Time-dependent drainage of radiotracer into multiple nodes has been reported (Glass et al., 1998). This allows non-sentinel nodes to become radioactive, which may mislead the surgeon to remove non-sentinel nodes but inadvertently leave behind the true sentinel nodes (Glass et al., 1998; Morton and Bostick, 1999). Thus, lymph nodes that are declared to be sentinel nodes by the surgeon may not be the true sentinel nodes; however, precise examination of these supposedly sentinel nodes may find them truly histopathologically negative. Additionally, an inherent difficulty with pathologic evaluation of sentinel nodes is that nodes identified and declared by the surgeon as sentinel nodes cannot be histopathologically confirmed, unless metastases are present.

Third, histopathologic evaluation of sentinel nodes may erroneously label sentinel nodes as tumor-negative when micrometastases are actually present. Neither isosulfan blue or radiocolloid is retained in sentinel nodes after processing, and so these agents cannot be identified by light microscopy. This histopathologic shortcoming of LM/SL could be mitigated if the sentinel nodes were stained with a mapping agent that remains in the tissue after histopathologic processing. Upon re-evaluation of sentinel nodes by sectioning and immunohistochemical staining of additional levels in patients with recurrent nodal melanoma after LM/SL, it is often the case that micrometastases were unappreciated at the initial examination (Miliotes et al., 1996). Therefore, any measure which can decrease the false negative rate or the histopathological error rate would potentially decrease the same basin recurrence after removal of tumor-free sentinel nodes.

Thus, there exists a need for improved methods for sentinel lymph node mapping. These improved methods should not exhibit the rapid washout of dyes or the time-dependent drainage of radiotracers. In addition, improved methods of histopathological confirmation of sentinel nodes and identification of tumor cell micrometastases in the sentinel node following lymphadenectomy is needed to promote better survival among this subset of patients.

SUMMARY OF THE INVENTION

The present invention describes materials and methods for the identification of sentinel lymph nodes by the surgeon and the pathologist and the presence or absence of lymph node metastases as an important prognostic factor in early stage cancers of all types. The present invention further defines a region of the sentinel lymph node that is identifiable by the surgeon and pathologist and is most likely to contain metastases.

The invention first provides a method of identifying a disease-associated lymph node in an excised tissue sample, comprising, administrating to a subject at least one fluid composition comprising of from about 0.1% carbon particles to about 6.0% carbon particles, excising at least one tissue sample suspected of comprising at least one lymph node, identifying a lymph node by the accumulation of said carbon particles, and; identifying, diagnosing, staging or predicting the presence of neoplastic tissue in said lymph node. As used herein certain embodiments, "fluid" means a liquid composition, such as a solution, a suspension, an emulsion and the like. However, in particular aspects, a suspension of carbon particles is preferred. In certain embodiments, the concentration of the carbon particles may vary. In specific aspects, the carbon particle concentration may be about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.10%, about 1.20%, about 1.30%, about 1.40%, about 1.50%, about 1.60%, about 1.70%, about 1.80%, about 1.90%, about 2.00%, about 2.10%, about 2.20%, about 2.30%, about 2.40%, about 2.50%, about 2.60%, about 2.70%, about 2.80%, about 2.90%, about 3.00%, about 3.10%, about 3.20%, about 3.30%, about 3.40%, about 3.50%, about 3.60%, about 3.70%, about 3.80%, about 3.90%, about 4.00%, about 4.10%, about 4.20%, about 4.30%, about 4.40%, about 4.50%, about 4.60%, about 4.70%, about 4.80%, about 4.90%, about 5.00%, about 5.10%, about 5.20%, about 5.30%, about 5.40%, about 5.50%, about 5.60%, about 5.70%, about 5.80%, about 5.90%, to about 6.0%, and any range derivable therein. As used herein, "any range derivable therein" means a range selected from the numbers described in the specification. For example, in non-limiting examples, the carbon particle concentration range may be of from about 0.15% to about 5.0%, about 0.15% to about 4.0%, about 0.15% to about 3.0%, about 0.15% to about 2.0%, about 0.15% to about 1.0%, about 0.2% to about 1.0%, about 0.3% to about 1.0%, about 0.4% to about 1.0%, or about 0.5% to about 1.0%.

In other embodiments, the size of the carbon particle may vary. In specific aspects, the carbon particle size (i.e., average diameter) may be about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.00, about 1.10, about 1.20, about 1.30, about 1.40, about 1.50, about 1.60, about 1.70, about 1.80, about 1.90, about 2.00, about 2.10, about 2.20, about 2.30, about 2.40, about 2.50, about 2.60, about 2.70, about 2.80, about 2.90, about 3.00, about 3.10, about 3.20, about 3.30, about 3.40, about 3.50, about 3.60, about 3.70, about 3.80, about 3.90, about 4.00, about 4.10, about 4.20, about 4.30, about 4.40, about 4.50, about 4.60, about 4.70, about 4.80, about 4.90, about 5.00, about 5.10, about 5.20, about 5.30, about 5.40, about 5.50, about 5.60, about 5.70, about 5.80, about 5.90, to about 6.0 microns, and any range derivable therein. For example, in specific aspects, the carbon particle size range may be of from about 0.1 and about 6.0, about 0.2 to about 4.0, about 0.2 to about 2.0, about 0.2 to about 1.0, or about 0.3 to about 0.8 microns in diameter. In other aspects, the carbon particle size range is less than about 0.2 microns in diameter.

In certain embodiments, the carbon particles comprise carbon black. In specific aspects, the carbon particles may comprise, but are not limited to, channel black, thermal black or furnace black. In other aspects, the carbon black particles are neutral, acidic or basic.

In some preferred embodiments, the composition further comprises at least one additional compound. In specific aspects, the at least one additional compound is a dye. In some aspects, the dye may comprise an anionic dye. In certain aspects, the dye may comprise, but is not limited to, is an acid dye, a basic dye or a direct dye. In particular facets the direct dye may comprise, but is not limited to, Paper Yellow GG (CI Direct Yellow 131), Direct Scarlet 4BS (CI 29160), Congo Red (CI 22120), Violet BB (CI 27905), Direct Sky Blue 5B (CI 24400), Pentamine, Phthalocyanine Blue (CI 74180), Black G (CI 35255) or Deep Black XA (CI Direct Black 154).

In particular facets, the dye may comprise Tartrazine (CI 19140), Quinoline Yellow (CI 47005), Eosin (CI 45380), Acid Phloxine (CI 45410), Erythrosine (CI 45430), Sunset Yellow FCF (CI 15985), Acid Violet 5B (CI 42640), Patent Blue AF (CI 42080), Brilliant Cyanine 6B (CI 42660), Acid Brilliant Blue FCF (CI 42090), Naphthalene Green VSC (CI 44025) or Acid Blue Black 10B (CI 20470). In other facets, the dye is isosulfan blue, guajazulen blue, patent blue V, pentamine or Direct Sky blue, or other dye which travels through the lymphatic system.

In other embodiments, the total concentration of the non-carbon particle, at least one dye, may vary. In specific aspects, the total concentration of dye(s) in the composition may be about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.10%, about 1.20%, about 1.30%, about 1.40%, about 1.50%, about 1.60%, about 1.70%, about 1.80%, about 1.90%, about 2.00%, about 2.10%, about 2.20%, about 2.30%, about 2.40%, about 2.50%, about 2.60%, about 2.70%, about 2.80%, about 2.90%, about 3.00%, about 3.10%, about 3.20%, about 3.30%, about 3.40%, about 3.50%, about 3.60%, about 3.70%, about 3.80%, about 3.90%, about 4.00%, about 4.10%, about 4.20%, about 4.30%, about 4.40%, about 4.50%, about 4.60%, about 4.70%, about 4.80%, about 4.90%, about 5.00%, about 5.10%, about 5.20%, about 5.30%, about 5.40%, about 5.50%, about 5.60%, about 5.70%, about 5.80%, about 5.90%, about 6.0%, about 6.10%, about 6.20%, about 6.30%, about 6.40%, about 6.50%, about 6.60%, about 6.70%, about 6.80%, about 6.90%, about 7.00%, about 7.10%, about 7.20%, about 7.30%, about 7.40%, about 7.50%, about 7.60%, about 7.70%, about 7.80%, about 7.90%, about 8.00%, about 8.10%, about 8.20%, about 8.30%, about 8.40%, about 8.50%, about 8.60%, about 8.70%, about 8.80%, about 8.90%, about 9.00%, about 9.10%, about 9.20%, about 9.30%, about 9.40%, about 9.40%, about 9.50%, about 9.60%, about 9.70%, about 9.80%, about 9.90%, to about 10.00%, and any range derivable therein. In other embodiments, the total concentration of the non-carbon particle, at least one dye, may vary in molar concentration. In specific aspects, the total molar concentration of dye(s) in the composition may be about 0.10 mM, about 0.15 mM, about 0.20 mM, about 0.25 mM, about 0.30 mM, about 0.35 mM, about 0.40 mM, about 0.45 mM, about 0.50 mM, about 0.55 mM, about 0.60 mM, about 0.65 mM, about 0.70 mM, about 0.75 mM, about 0.80 mM, about 0.85 mM, about 0.90 mM, about 0.95 mM, about 1.00 mM, about 1.10 mM, about 1.20 mM, about 1.30 mM, about 1.40 mM, about 1.50 mM, about 1.60 mM, about 1.70 mM, about 1.80 mM, about 1.90 mM, about 2.00 mM, about 2.10 mM, about 2.20 mM, about 2.30 mM, about 2.40 mM, about 2.50 mM, about 2.60 mM, about 2.70 nM, about 2.80 mM, about 2.90 mM, about 3.00 mM, about 3.10 mM, about 3.20 mM, about 3.30 mM, about 3.40 mM, about 3.50 mM, about 3.60 mM, about 3.70 mM, about 3.80 mM, about 3.90 mM, about 4.00 mM, about 4.10 mM, about 4.20 mM, about 4.30 mM, about 4.40 mM, about 4.50 mM, about 4.60 mM, about 4.70 mM, about 4.80 mM, about 4.90 mM, about 5.00 mM, about 5.10 mM, about 5.20 mM, about 5.30 mM, about 5.40 mM, about 5.50 mM, about 5.60 mM, about 5.70 mM, about 5.80 mM, about 5.90 mM, about 6.0 mM, about 6.10 mM, about 6.20 mM, about 6.30 mM, about 6.40 mM, about 6.50 mM, about 6.60 mM, about 6.70 mM, about 6.80 mM, about 6.90 mM, about 7.00 mM, about 7.10 mM, about 7.20 mM, about 7.30 mM, about 7.40 mM, about 7.50 MM, about 7.60 mM, about 7.70 mM, about 7.80 mM, about 7.90 mM, about 8.00 mM, about 8.10 mM, about 8.20 mM, about 8.30 mM, about 8.40 mM, about 8.50 mM, about 8.60 mM, about 8.70 mM, about 8.80 mM, about 8.90 mM, about 9.00 mM, about 9.10 mM, about 9.20 mM, about 9.30 mM, about 9.40 mM, about 9.40 mM, about 9.50 mM, about 9.60 mM, about 9.70 mM, about 9.80 mM, about 9.90 mM, to about 10.00 mM, and any range derivable therein. In a non-limiting example, the total dye concentration of the composition may be of from about 0.1 to about 10 mM. Of course, more than one dye may comprise the total dye concentration of the composition.

In preferred facets, the dye is isosulfan blue. In certain facets, the concentration of isosulfan blue is about 0.10%, about 0.15%, about 0.20%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, about 1.00%, about 1.10%, about 1.20%, about 1.30%, about 1.40%, about 1.50%, about 1.60%, about 1.70%, about 1.80%, about 1.90%, about 2.00%, about 2.10%, about 2.20%, about 2.30%, about 2.40%, about 2.50%, about 2.60%, about 2.70%, about 2.80%, about 2.90%, to about 3.00%, and any range derivable therein. In a non-limiting example, isosulfan blue is about 0.1% to about 1.0%. In another example, the concentration of isosulfan blue is about 0.25% to about 1%. In other examples, the concentration of isosulfan blue is about 0.5% to about 0.9%. In other embodiments, the composition comprises carbon dye, radiolabeled sulfur colloid and isosulfan blue dye.

In certain embodiments, the at least one additional compound comprises a diagnostic aid. In preferred aspects, the diagnostic aid is Fluorescein or Fluorescein Sodium.

In other embodiments, the at least one additional compound is a radionucleotide tracer. In specific facets, the radionucleotide tracer is technetium-labeled sulfur or albumin colloid, antimony chloride, or other colloidal radionucleotide that travels through the lymphatic system. In some embodiments, the at least one additional compound is a receptor binding compound, an antibody or a locator.

In certain embodiments, the administering of the composition is to the lymphatic region surrounding a neoplastic tissue. In specific facets the neoplastic tissue is a melanoma, lung carcinoma, neuroblastoma, pheochromocytoma, colon, prostate, renal carcinoma, breast carcinoma, esophageal, gastric, pancreatic, oropharyngeal cancer or another neoplasm that metastasizes by the lymphatic channels. In preferred aspects, the neoplastic tissue is a melanoma or a breast carcinoma. In specific facets, the mode of administration is subcutaneous, intramuscular, intralesional, intradermal, intraperitoneal, parenteral, oral, nasal, buccal, rectal, vaginal or orthotopic. In other facets, the time between administering and detecting the carbon particles is about 1 minute, about 2 minutes, about 3 minutes, about 4 minutes, about 5 minutes, about 7 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 100 minutes, about 110 minutes, about 120 minutes, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours (about 1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours (about 2 days), and any range derivable therein. In a non-limiting example, the range of time between administering and detecting the carbon particles is between about 5 minutes and about 60 minutes. In another example, the range of time between administering and detecting the carbon particles is between about 1 minute and about 2 days.

In certain embodiments, the subject is an animal, such as a mammal. In preferred aspects, the subject is a human.

In certain embodiments, the tissue sample is removed by a lymphadenectomy. In other embodiments, a lymph node is further identified by using a hematoxylin-eosin histopathological technique, an immunohistochemical technique, spectroscopy or a cancer staging technique. In certain aspects, the method further comprises a microscopic examination of the lymph node.

In particular embodiments, the identifying a lymph node identifies at least one sentinel lymph node. In some aspects, the identifying a sentinel lymph node further comprises histopathology. In certain facets, the histopathology further comprises assessment of carbon particle accumulation in a subregion of the sentinel lymph node. In other facets, the histopathology further comprises identification, diagnosing, staging, or predicting the presence of neoplastic tissue in the sentinel lymph node. In particular facets, a subject who has evidence of micrometastasis in the sentinel node undergo a subsequent lymphadenectomy.

The invention also provides a method of identifying a disease-associated lymph node in an excised tissue sample, comprising, administrating to a subject at least one fluid composition comprising of from about 0.1% carbon particles to about 6.0% carbon particles and isosulfan blue, excising at least one tissue sample suspected of comprising at least one lymph node, identifying a lymph node by the accumulation of said carbon particles, and; identifying, diagnosing, staging or predicting the presence of neoplastic tissue in said lymph node.

The invention provides a method of identifying a disease-associated lymph node in an excised tissue sample, comprising, administrating to a subject at least one fluid composition comprising of from about 0.1% carbon particles to about 6.0% carbon particles and isosulfan blue, excising at least one tissue sample suspected of comprising at least one lymph node, identifying a lymph node by the accumulation of said carbon particles, and; identifying, diagnosing, staging or predicting the presence of neoplastic tissue in said lymph node.

The present invention further describes a method for identifying a disease-associated sentinel lymph node in a subject comprising the steps of administering a carbon particle suspension in combination with a second compound to the lymphatic region surrounding a neoplastic tissue and locating the sentinel lymph node by detecting the accumulation of carbon particles in conjunction with the second compound. In preferred embodiments, the second compound is a dye or a radionucleotide tracer. The dye can be isosulfan blue, guajazulen blue, patent blue V, pontamine or skyblue, or other dyes which travel through the lymphatic system. The radionucleotide tracer can be a technetium-labeled sulfur or albumin colloid, antimony chloride, or other colloidal radionucleotides that travel through the lymphatic system. In preferred embodiments the subject with the neoplastic tissue is human.

Also described are methods and compositions wherein the detecting the accumulation of carbon particles occurs in the sentinel nodes removed by a lymphadenectomy. This can be combined with histopathology of neoplastic tissue and associated lymph nodes. In preferred embodiments, the histopathology further comprises identification, diagnosing, staging, or predicting the presence of neoplastic tissue in the regional or sentinel lymph node. In preferred embodiments, the histopathology further comprises assessment of carbon particle accumulation in a subregion of the sentinel lymph node.

The present invention also describes a method of identifying a disease-associated lymph node in an excised tissue sample following administration of a carbon particle suspension to a subject comprising identifying the sentinel lymph node by the accumulation of said carbon particles and identifying, diagnosing, staging or predicting the presence of neoplastic tissue in said sentinel lymph node. In preferred embodiments, the histopathology further comprises assessment of carbon particle accumulation in a subregion of the sentinel lymph node.

As used herein the specification, "a" or "an" may mean one or more. As used herein in the claim(s), when used in conjunction with the word "comprising", the words "a" or "an" may mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The file of this patent contains at least one drawing executed in color. Copies of this patent with color drawing(s) will be provided by the Patent and Trademark Office upon request and payment of the necessary fee. Color drawings will be included in the drawings incorporated herein as they are histological photographs.

DESCRIPTION OF ILLUSTRATIVE EMBODIMENTS

Figure 1:
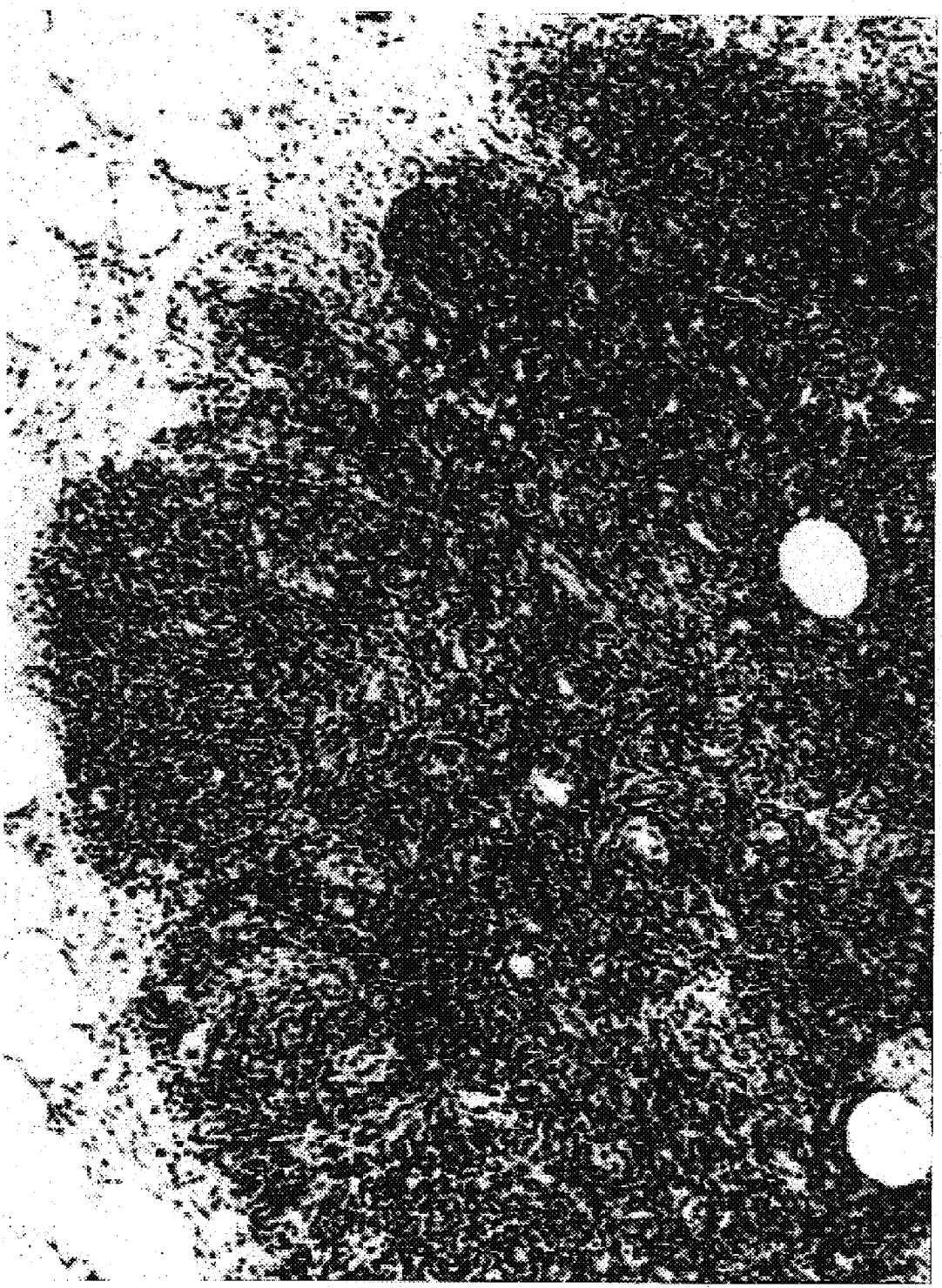
FIG. 1. Low power view of a A & E stained lymph node, showing the large area to be searched for cancer cells.
Figure 2:
FIG. 2. Mid-power view showing distribution of carbon particles in the lymph node, which mark the node to look for cancer cells, and confirm by histopathology that the node is a sentinel node.
Figure 3:
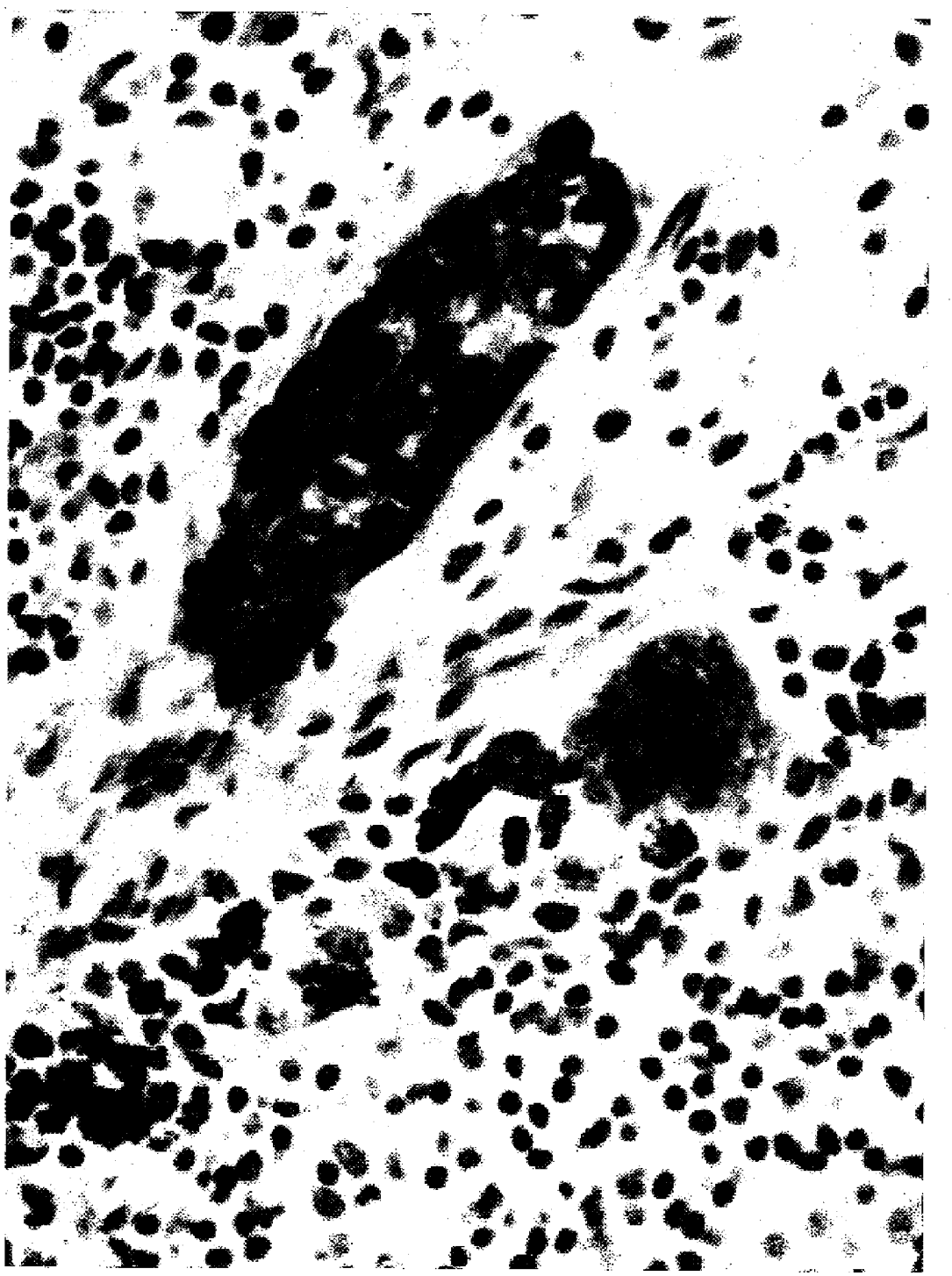
FIG. 3. High power view showing melanoma cancer cells adjacent to carbon particles.

The single most important prognostic factor for patients with early-stage melanoma and other solid neoplasm is the tumor status of the regional nodes draining the primary tumor. Until recently, the only method to identify the regional nodal metastasis was complete lymph node dissection followed by pathologic examination of each excised node using hematoxylin and eosin (H&E) staining. However, this technique samples only a small percentage of each node and therefore underestimates the true frequency of nodal metastasis. The sentinel lymph node within the regional node associated with a tumor is a critical site for identification, diagnosing, staging or predicting the presence of nodal metastasis. However, even if the true sentinel lymph node is identified by the surgeon, the microanatomy of the sentinel node results in micrometastases being confined to only a small section of the node. This results in the pathologist often times missing a small micrometastasis in the peripheral sinus of one section of the node unless multiple serial sections are taken throughout that node.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is involved with the blood vascular system in developing the immune response of the lymphocytes and other cells. Lymph flows within the system as a consequence of a variety mechanisms of organ and tissue dynamics.

For certain cancers, metastasis occurring in consequence of lymph drainage will result in an initial location or positioning of neoplastic cells at certain lymph nodes typically deemed "sentinel nodes" within a pertinent regional lymph drainage basin. Some cancers, for example, melanomas, have been observed to exhibit variability in lymphatic drainage patterns emanating from different portions of the body. Other cancers, such as those encountered in the breast will evidence somewhat more predictable nodal involvement.

In designing forms of cancer disease management, therefore, efforts are directed to the identification of affected lymph nodes. For melanomas, it has been a more recent practice to identify the pertinent disease associated drainage basin or regional nodes along with an evaluation of the extent of lymph involvement with micrometastasis. A pre-surgical step investigative procedure undertaken in melanomas involves lymphatic mapping in the form of lymphoscintigaphy. The clinician is able to generate a two-dimensional image by injecting into the tumor site a tracer, for example, sulfur colloid labeled with technetium 99-m ($^{99m}T_c$). The path of drainage and the location of the proper drainage basin is identified by the region of radioactivity at the pertinent regional lymph nodes. Sentinel nodes then are removed and submitted for pathology evaluation. The success of intraoperative lymphatic mapping depends on accurate identification of the sentinel node by the nuclear medicine practioner, its accurate removal by the surgeon and the accurate identification of metastatic tumor cells in the sentinel node.

Carbon dye has been used in a number of clinical situations. It is commonly used for endoscopically marking colon polypectomy sites (Fennerty et al., 1992; Botoman et al., 1994) and for tattooing skin to demarcate the fields of external beam radiation. Particularly interesting is the use of carbon particles to delineate lymphatic drainage in stomach, pancreas, and breast cancer. Eriguchi et al. (1991) used preoperative endoscopic injections of Chinese ink and identified microscopic carbon particles in the resected lymph nodes of upper and middle third gastric cancers. Kitamura et al. (1995) utilized endoscopic injections of a mixture of activated carbon particles (CH-40) that stains the serosa and enters the lymphatics, to delineate the extent of lymphadenectomy and to guide resection margins for early gastric cancer. Nagakawa et al. (1994) injected the head of the pancreas in patients undergoing pancreaticoduodenectomy to document preferential lymphatic drainage to area 16 in the retroperitoneal nodes. More recently, Yokota et al. (2000) injected the breast in patients undergoing modified radical mastectomy as a method to increase the number of resected axillary lymph nodes. Carbon dye has been used as an adjunct to aid intraoperative idenification of lymph nodes to assist lymphadenectomy for some cancers (Sawai et al., 1989; Takahashi et al., 1987; Yoshida et al., 1988; Kodama et al., 1988; Sawai et al., 1996; Okamoto et al., 1999; Carbon particles and radioisotopes have been injected into pancreas cancer patients to trace the uptake of concentrated carbon particles and radioisotopes in regional lymph nodes (Nagakawa et al., 1994). Additionally, mytomycin C, aclarubicin, methotrexate and pepleomycin have been targeted to lymph nodes associated with various cancers (Toshio et al., 1991; Takahashi et al., 1991; Hagiwara et al., 2000; Irnanishi et al., 1995; Ohyama et al., 1995; Hagiwara etal., 1998; Hagiwara et al., 1987).

The results described herein demonstrate the use of carbon dye, and particularly carbon dye as an adjunct to isosulfan blue dye and radiocolloid for LM/SL in melanoma to facilitate histopathologic evaluation of sentinel nodes, rather than improve intraoperative identification of lymph nodes. The present invention describes the use of carbon black suspensions for sentinel lymph node identification and identification of which region of the node is likely to contain micrometastases. In certain embodiments, the present invention uses a carbon particle suspension for histopathologic confirmation of the sentinel lymph node through deposition of carbon within that node.

The present invention also demonstrates the surprising ability of relatively dilute concentrations of carbon particles to specifically identify sentinel lymph nodes in histopathologic studies. An animal model was used to compare the lymphatic mapping accuracy of carbon dye with that of isosulfan blue dye, the standard agent for intraoperative visualization of the sentinel lymph node. Although isosulfan blue dye and full-strength carbon dye each stained all sentinel nodes, the latter obscured histologic detail. The combination of 2.5% carbon dye, 7.5% saline and 90% isosulfan blue dye stained all sentinel nodes and did not interfere with histologic evaluation. Carbon dye exhibited significantly less intradermal diffusion than isosulfan blue dye. No toxicity or side effects associated with the use of carbon dye were observed. Carbon dye allows histopathologic confirmation of sentinel lymph nodes identified by isosulfan blue dye.

The addition of carbon particles to isosulfan blue for LM/SL in human patients with melanoma is a novel method to histopathologically confirm sentinel node retrieval. LM/SL removes a number of nodes that are defined as sentinel nodes. Example 2 describes one embodiment of the present invention, wherein after the surgeon has removed sentinel nodes identified by the combination of isosulfan blue/India ink and radiocolloid, the pathologist can verify their status by identifying carbon particles. Non-sentinel nodes, either those removed at LM/SL or after complete lymph node dissection were almost always free of carbon particles. The only tumor-positive sentinel nodes were those that contained carbon particles, which is strong evidence that carbon particles reside within the true sentinel nodes. Therefore, ostensible sentinel nodes labeled by the surgeon because they are radioactive or blue may in fact be non-sentinel nodes because of the absence of carbon particles.

As described herein for human patients, the addition of India ink to the blue dye/radiocolloid combination does not improve the intraoperative rate of sentinel node identification; rather, it refined the histopathological distinction between sentinel and non-sentinel nodes removed at LM/SL. The presence of carbon particles correlated with the presence of sentinel node metastases. Carbon particles are readily identifiable as black pigment within macrophages compared to the brown pigment of melanin. Melanoma micrometastases reside in the subcapsular sinus, and the carbon particles were invariably found adjacent to metastatic cells. This subcapsular location of carbon particles is quite different than the location of carbon particles identified in the lymph nodes of patients with skin tattoos, inhaled anthracotic pigment, or synthetic joints; in these other scenarios, carbon particles reside in macrophages found in the lymph node medulla (Anderson et al., 1996; Strom et al., 1989; Margevicius et al., 1996). Identifying carbon particles in one area of the subcapsular sinus can aid the pathologist to search for micrometastases in the same area. In all cases observed herein, the micrometastases were accompanied by carbon particles.

The similar location that carbon particles and metastases share in sentinel nodes is important because an increased detection rate of micrometastases oil light microscopy may reduce the risk of regional basin recurrence after LM/SL. Essner et al., (1999) reported a same-basin recurrence of 4.8% in 267 histologically node-negative patients who underwent LM/SL after a median follow-up 45 months. Gershenwald et al. (1998) reported a similar recurrence rate of 4.1% in a previously mapped basin in 243 patients with histologically negative sentinel node and had LM/SL only. However, occult sentinel node metastases were identified on histopathologic re-evaluation of the apparently tumor-free sentinel nodes in the majority of patients who recurred. Both of these studies used routine histopathologic evaluation in addition to immunohistochemistry on first evaluation. Carbon dye may help to decrease the chance that a pathologist may overlook micrometastases on first histopathologic evaluation.

As the disclosures herein demonstrate, carbon particles are readily identifiable in the majority of sentinel nodes, and they are rarely present in non-sentinel nodes removed at LM/SL. Carbon particles facilitate histopathologic evaluation by directing the pathologist to the sentinel nodes most likely to contain tumor. Histopathologic verification of sentinel nodes by identifying carbon particles may help to decrease the rate of missed micrometastases, and may decrease the same basin recurrence rate after LM/SL for sentinel node-negative melanoma.

I. Neoplastic Tissue and Lymph Nodes

The present invention can be used for lymph node mapping in association with a number of cancers. Examples include lung carcinoma, melanoma, neuroblastoma, pheochromocytoma, colon, prostate and renal carcinoma, breast carcinoma, esophageal, gastric, pancreatic, oropharyngeal cancer and other neoplasms that metastasize via the lymphatics. Preferred cancers are melanoma, breast cancer and solid tissue cancer.

Melanomas are among the most serious manifestations of skin cancer and lead to a greater number of fatalities than any other form of skin cancer. Melanomas can metastasize through the lymphatic system to regional nodes and then via the blood to secondary sites on the skin or in the liver, lungs and brain. Whereas the prognosis for superficial spreading melanomas can be quite good, there is a much poorer prognosis for nodular melanomas in which distant metastases frequently form.

Breast cancer is a major cause of death for women, and estrogen receptors have been reported to play a major role in the development and growth of breast tumors. Deprivation of estrogen is one of the clinically effective methods for the treatment of breast cancer patients. Several growth factors such as insulin-like growth factor I (IGF-I), transforming growth factors (TGF-$\alpha$ and -$\beta$), epidermal growth factor (EGF), and platelet-derived growth factors have been shown to be involved in the growth and progression of human breast cancer cells. Some growth factors such as TGF-$\beta$ act as inhibitors of tumor growth. Despite the development of numerous antiestrogen and other drugs, the clinical utility of antiestrogen is limited due to resistance by the tumor cells.

An evaluation of the presence or absence of tumor metastasis or invasion has been a major determinant for the achievement of an effective treatment for cancer patients. Studies have determined that about 30% of patients with essentially newly-diagnosed cancer will exhibit clinically detectable metastasis. Of the remaining 70% of such patients who are deemed "clinically free" of metastasis, about one-half are curable by local tumor therapy alone (Sugarbaker, 1981). The remaining patients will have clinically occult (undetected) micrometastasis that ultimately become manifest.

Patient management for staging purposes for the case of cutaneous melanoma is highly predicated upon determinations of lymph involvement. A number of factors are involved in the prognosis of the disease including location, tumor thickness, level of invasion, growth patterns, and of particular importance, the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial debate exists between investigators as to whether or not elective lymph node dissection or lymphadenectomy is an appropriate therapy. Elective lymphadenectomy has the major advantage of treating a nodal metastasis at a relatively early stage in its natural history when the tumor burden is low. On the other hand, such an approach may subject patients to surgery which would otherwise have been unnecessary.

For cancers such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer (DeVita et al., 1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by fatty tissue and visualization of them is limited. Dissection will pose risks, such as cutting the long thoracic nerve, the thoracic-dorsal nerve, the nerve to the pectoralis major or the axillary vein. Morbidity may occur in some cases due to regional node removal and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below. However, this requires acurate identification of sentinel lymph nodes.

II. Sentinel Lymph Node

Morton et al. (1992) described a procedure designed to identify that lymph node nearest the site of a melanoma and within the pertinent lymph drainage basin. Such a node, being on the most direct drainage pathway, will present the most likely site of early metastasis and is referred to as the "sentinel node." Thus, by carrying out only a limited dissection specific to this node, and performing pathologic analysis thereof, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively stained with blue color and readily identified. Thus, the sentinel draining lymph node of each primary melanoma is isolated and removed. By examining the sentinel nodes, for example by frozen or permanent section using routine hematoxylin-eosin histopathological techniques, as well as immunohistochemical techniques, only those patients who have evidence of micrometastasis in the sentinel draining node are subject to subsequent lymphadenectomy (Morton et al., 1992; Uren et al., 1993).

The approach of Guiliano et al. (1994) also has been undertaken to moderate the otherwise somewhat radical axillary lymph node dissection common in staging breast cancer. Through the utilization of the vital dyes in conjunction with the lymph drainage system from primary breast minor, less radical sentinel node based procedures may result in adequate axillary staging and regional control. With the procedure, in general, a vital blue dye is injected into the breast mass and surrounding breast parenchyma. Following a relatively short interval, a transverse incision is made. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes (Guiliano et al., 1994).

III. Cancer Staging and Evaluation

The present invention is beneficial for cancer staging and evaluation. Carbon black identification of the sentinel lymph node will aid in the determination of the presence of metastatic cells in the disease associated lymph nodes. In determining how to treat a particular cancer, it also is important to stage (or grade) it, at the microscopic level, from tissue removed at the time of surgery. The purpose of examining the resected tissues in this way is to determine, at the microscopic level, the extent of the local spread of the cancer, whether the margin between the resected cancerous mass and the presumably healthy tissue that is left behind is free of cancer, and/or whether there is spread of cancer cells to regional lymph nodes. The microscopic level examination of tissues removed in surgery is an index of whether or not cancer cells have spread beyond the primary cancerous mass and the cancer is likely to grow again, either locally or at distant sites.

The microscopic examination of cancerous tissue, and the tissue surrounding it that is believed normal tissue, preferably provides information as to whether there is local extension of the primary cancerous mass. This examination also provides a road map to determine which tissue in the patient may still be affected. The microscopic examination of lymph node tissue in the area around the cancerous mass, typically resected with the cancerous mass, is a factor in determining the success of the surgery and the therapy to subsequently treat the patient.

For example, in colon cancer, which is the second most common cancer in the United States and the developed world, the prognosis for survival is inversely related to the extent to which cancer cells penetrate the luminal surface of the colon into (or through) the colon wall or has spread to the regional lymph nodes. For a given depth of cancer cell penetration into the colon wall, the prognosis degrades as the number of regional lymph nodes with cancer cells increases. The relationships between the local extent of cancer and post-surgery prognosis apply to most cancers, e.g., breast, prostate, head, and neck cancer. As such, the staging of cancer by microscopic level examination of lymph node tissues removed during surgery is an important part of the medical treatment of cancer patients.

Presently, the staging of cancer is performed by microscopic level examination of the removed tissue. This method does not provide sufficient accuracy to predict the likelihood that cancer has spread beyond the immediate site of the primary tumor. Thus, it does not provide assurance that all the cancer cells have been removed from the patient. Obviously, there needs to be a practical way to obtain such information.

There is only a general relationship between prognosis and the extent of the local extension of cancers; however, this relationship is not absolute. Frequently, local and/or distant (metastatic) recurrences of cancers occur in patients whose tissue sections have margins that appear free of cancer cells as do the regional lymph nodes. The inability to properly stage cancer based on examination of the removed tissue results in the cancer cure rates being quoted in terms of long-term survival, e.g., 5 or even 10 years of disease free time after surgery.

Pathologists who examine the removed tissue have no adequate means to determine whether all the cancer was in fact removed from the patient. Moreover, they do not have a method to accurately stage the tissue that they have. In attempts to derive the needed accuracy for the staging process, pathologists have developed morphologic criteria to hopefully enhance the accuracy of predicting the biologic behavior of cancers. This process was intended to distinguish between small, apparently contained cancers that will not recur and those cancers that will recur. The prediction of recurrence of the cancer is based of the morphology of the cancer cells and how they are organized.

The classification of cancer cells on the basis of their content of DNA and other biochemical measurements of cancer cells have not augmented significantly the predictive value of examining resected cancer tissues. As such, one of the problems of oncology and pathology is the well-known phenomena that some cancers behave aggressively to kill the patient while others that appear very similar, and which may be found in the same organ, behave in a relatively benign way, i.e., do not recur after the primary cancerous mass is removed.

Cancer staging has been complicated by the fact that it evolved over half a century. Many investigators agree that the most important independent pathologic factor for survival or recurrence after potentially curative surgery is the stage of cancer, which is determined by the depth of penetration into the adjoining area and the presence and number of positive lymph nodes. Other independent factors for survival have included gross appearance, lymphatic vessel invasion, blood vessel invasion, nucleolar organizer regions, character of invasive margin and tumor type, number of mast cells, nuclear shape, sedimentation rate and leukocytosis, lymphocytic infiltration, obstruction, perforation, and rectal bleeding, filtration, infiltrating border (lateral margins), age, grade, venous invasion, gender, obstruction, ploidy, and preoperative carcinoembryonic antigen.

A. Cancer Staging Systems

Several examples of cancer staging systems exist. One such staging system was the Dukes classification, named after a British pathologist who conducted extensive studies, in the 1930's, on the local invasion and lymphatic spread of rectal cancer. Dukes originally classified rectal tumors from A to C, with stage A indicating penetration into but not through the bowel wall, stage B indicating penetration through the bowel wall, and stage C indicating involvement of lymph nodes, regardless of bowel wall penetration. This system had the virtue of being simple and predictive of prognosis. It has since been modified many times, to reflect finer levels of penetration and nodal metastases, and has been extended to include both colon and rectum.

A second staging system, the TNM classification system, ranks the primary tumor (T), the regional lymph nodes (N), and distant metastases (M). For example, a T1 tumor invades the submucosa, a T2 tumor the muscularis propria, etc.; N1 indicates an absence of regional node metastases, whereas N1 correlates with 1–3 positive nodes and N2 correlates with 4 or more positive nodes, etc.; and M0 indicates an absence of distant metastases, while M1 indicates that such metastases are present. Any given case of colorectal cancer can thus be described in terms of its TNM status, i.e., $T_x N_x M_x$.

Another staging system, called Astler-Coller, allowed separation of wall penetration and nodal status. The Gunderson-Sosin modification of the Astler-Coller staging system subdivided T3 tumors into those with microscopic ($B2_m$ or $C2_m$) and gross ($B2_{m+g}$ or $C2_{m+g}$) penetration of tumor through the bowel wall. In all pathologic staging systems, particularly those applied to rectal cancer, the abbreviations (m) and (g) may be used: (m) to denote microscopic transmural penetration; (g) or (m+g) to denote transmural penetration visible on gross inspection and confirmed microscopically.

In 1988, the American Joint Committee on Cancer (AJCC) and the Union Internationale Contra le Cancer (UICC) adopted a joint TNM classification scheme taking into account the number of positive nodes and also free mesothelial penetration.

Yet another classification system was introduced in 1987 by Jass and colleagues. Using a Cox regression analysis, they found that the number of positive nodes, whether the invasive border was pushing or infiltrative, the presence of a conspicuous lymphocytic infiltrate, and the absence or presence of transmural penetration were independent prognostic factors. Because the Jass staging system is far more complicated than the modified Dukes and TNM systems, it has not been formally accepted by the National Surgical Adjuvant Breast and Bowel Project (NSABP) or other major clinical groups. The Gastrointestinal Tumor Study Group (GITSG) has also developed a classification system, which shares some of the features of the Jass system.

B. Molecular Approaches to Cancer Staging

Research has established that the presence or absence of disease in cells and tissues is based on whether molecules are normal in-structure and whether a normal distribution of molecules is present in a given type of cell. This has led physicians to recognize that accurate diagnoses of disease may be based on a gathering and an evaluation of information at the molecular level in cells. As such, it has now become essential to perform molecular level analysis to diagnose diseases, like cancer, at early stages for the accurate detection of specific types of disease through the examination of cells and tissues.

Spectroscopy has some advantages over the use of chemical or molecular probes in that spectroscopy can make measurements without prior knowledge of the exact type of abnormality present. Further, results from spectroscopy may be obtained faster than when probes are used. It also has been surmised that vibrational spectroscopy is the most useful type for examination contemplated in the present invention. However, vibrational spectroscopic techniques have not been used for diagnosing disease.

Having resolved that vibrational spectroscopic techniques are useful for diagnosing disease, it becomes necessary to provide a method to practically apply those techniques. In order to apply vibrational spectroscopic techniques, it is principally necessary to understand the spectral characteristics of the cells that are being analyzed.

C. Biopsy and Evaluation of Disease-associated Lymph Nodes

Instruments are and techniques are known for tissue sampling in combination with the present invention. For example, U.S. Pat. No. 5,111,828 to Kornberg et al. discloses a percutaneous excisional breast biopsy device having a cannula, open distal and proximal ends, and a sharp cutting surface on the distal end. A stylet extends through the cannula and includes a distal puncturing end. A localization guide wire is used to direct the instrument to a biopsy site. The cannula is moved distally to cut a desired tissue specimen, after which a descending element is pushed to the distal end of the tissue specimen, then pulled proximally to sever the specimen completely from surrounding tissue.

A significant disadvantage of the Kornberg approach is that only one tissue sample may be obtained for each insertion of the instrument into the patient's body to the biopsy site. Once the descending element has been pulled to sever the tissue sample, there is no opportunity to repeat the procedure while the instrument remains in place. Also, no means is provided to ensure that tissue to be sampled is drawn toward the distal end of the cannula 2 (or "actively captured"), thereby reducing tissue sampling efficiency.

IV. Carbon Particles

"Carbon black" is the term used for the pulverized forms of carbon which are produced by incomplete combustion or thermic degradation of natural gas or mineral oil. Depending upon the method of production, different types of carbon black arise, namely so called channel black, furnace black and pyrolysis black (also called thermal black).

Channel black is characterized by a lower pH, a higher content of volatile constituents and fewer chain-like structures between the particles. It has the smallest particle size of all materials produced in industry and its particles are within colloidal size range. Its major field of use is as a reinforcement material in rubber, where it improves both the wear resistance and the oil resistance of the rubber.

Thermal black consists of relatively coarser particles and is primarily used as a pigment. Furnace black, which has been produced from natural gas, has a medium size, while the furnace black produced from oil may occur within a broad range of controlled particle sizes and is particularly suitable for reinforcing synthetic rubber. Furnace black is by far the most important form of carbon black and is used to a considerably larger extent than the other two. Also the present invention relates specifically to this type of carbon black.

Carbon black is commercialized in the form of a powder, or pellets or paste. The powder is kept in multi-walled paper bags or in lined barrels. Carbon black is used as an additive in rubber tires and other wear resistant rubber products. In plastics it is used as a reinforcing agent, as an opacifier, as a means for increasing the electrical conductivity and for absorbing ultraviolet light. Further, carbon black is used for instance in duplicating carbon, in ink ribbons for typewriters, in colour pigments and for influencing the weather.

The kind of the carbon black used as a raw material is not particularly restricted. Any of the above-described acidic carbon black, neutral carbon black and alkaline carbon black can be used. Specific examples of the carbon black include #10B, #20B, #30, #33, #40, #44, #45, #45L, #50, #55, #95, #260, #900, #1000, #2200B, #2300, #2350, #2400B, #2650, #2700, #4000B, CF9, MA8, MA11, MA77, MA100, MA220, MA230, MA600, MCF88 and the like manufactured by Mitsubishi Kagaku K.K.; Monarch 120, Monarch 700, Monarch 800, Monarch 880, Monarch 1000, Monarch 1100, Monarch 1300, Monarch 1400, Mogul L, Regal 99R, Regal 250R, Regal 300R, Regal 330R, Regal 400R, Regal 500R, Regal 660R and the like manufactured by Cabot K.K.; Printex A, Printex G, Printex U, Printex V, Printex 55, Printex 140U, Printex 140V, Special black 4, Special black 4A, Special black 5, Special black 6, Special black 100, Special black 250, Color black FW1, Color black FW2, Color black FW2V, Color black FW18, Color black FW200, Color black S150, Color black S160, Color black S170 and the like manufactured by Degussa K.K.; and the like.

The acidic carbon black is commercially available from Mitsubishi Kasei K.K. under the trade name of MA8, MA100, 2200B and 2400B, from Degussa K.K. under the trade name of Color carbon black FW200, Color black FW18, Color black S150, Color black S160, Color black S170, Printex U and Printex 1400, from Cabot K.K. under the trade name of Monarch 1300, Mogul L and Regal 400R, from Columbian Carbon K.K. under the trade name of Raven 1200, Raven 1220 and Raven 1225.

The neutral or basic carbon black is commercially available from Mitsubishi Kasei K.K. under the trade name of #33, #45, #45L, #10B, #4000B, #2300, #2400 and #900, from Degussa K.K. under the trade name of Color Furnace such as Printex 35, Printex 60, Printex 300, Printex A and the like, from Cabot K.K. under the trade name of Oil Furnace such as Regal 330R, Regal 300R, Regal SR and the like, from Columbian Carbon K.K. under the trade name of Raven 40, CONDUCTEX SC and MOLACCO LS.

A. Methods of Producing Carbon Black

Carbon black is produced by burning a mixture of air and oil to produce hot gases and then conducting the hot gases through tubes extending through a chamber of a heat exchanger. Heat exchange air is conducted through the chamber in a direction opposite the direction of gas flow, in heat-exchange relationship with the tubes, to pre-heat the air. The pre-heated air is then mixed with the oil to be burned. Prior to entering the chamber, the air is conducted within a hollow section of the wall structure of the heat exchanger to transfer heat from a hot end of the wall structure toward a cooler end thereof.

U.S. Pat. No. 5,891,414 describes a method for producing carbon black. More particularly, the present invention relates to a method for producing carbon black, by an oil furnace method, wherein small size particle carbon black is obtained with a high yield.

U.S. Pat. No. 5,861,447 An aqueous pigment ink composition comprising an oxidized carbon black obtained by wet-oxidation of a carbon black using a hypohalous acid and/or salt thereof, and a water-soluble cationic polymer or oligomer in an aqueous medium. The aqueous pigment ink composition of the present invention does not cause clogging in a nozzle when used for ink jet recording, enables smooth writing from a narrow pen tip, and provides a recorded image excellent in water resistance and light resistance and excellent in density and hue.

Japanese Examined Patent Publication No. 45581/1980 discloses a process for producing carbon black, wherein air for combustion is preheated by heat exchanger with the reaction product after quenching, for heat recovery, and a part of the preheated air is supplied to the reactor as an independent divided stream for the protection of the reactor wall. However, in this process, the introduction of the feedstock is limited to the center portion around the reactor axis, and no high temperature combustion gas stream will be formed along the reactor wall, whereby formation of a high temperature turbulent flow region essential for conducting the thermal cracking of the hydrocarbon feedstock with high efficiency, will be inadequate. Besides, the hydrocarbon feedstock is supplied from a feedstock supply nozzle in an axial direction held in the high temperature reactor, whereby it is necessary to provide a cooling jacket for the protection of the nozzle, thus leading to an extra heat loss. Furthermore, since the feedstock is introduced from the reactor axis, it takes time for the diffusion of the feedstock in the radial direction, whereby effective mixing can not be conducted at a high speed, thus leading to a decrease in the yield of carbon black.

Still further, Japanese Unexamined Patent Publication No. 183364/1986 discloses a process for producing carbon black by means of a carbon black production reactor, wherein a combustion chamber is provided with a gas inlet directed in a tangential direction, wherein a feedstock is introduced into its throat in a direction traversing the gas stream for thermal cracking. However, the high temperature combustion gas stream is a swirling stream, and it is incapable of forming an adequate high temperature turbulent flow region at the throat i.e. at the supply point of the feedstock, whereby it is impossible to form carbon black with high efficiency.

Japanese Examined Patent Publication No. 6203/1972 discloses a process for producing carbon black, wherein turbulence is created by a plurality of burners disposed at an angle of from 10 to 80 degree, to the reactor axis, and a hydrocarbon feedstock is supplied to intersect the turbulence. However, the reactor having the burners attached thereto has a truncated cone shape with its cross-sectional area gradually increasing towards the throat (diaphragm), whereby the turbulent flow obtained by the intersection of the combustion mixture streams diminishes towards the throat, whereby the turbulent flow energy of the combustion mixture streams and the turbulent flow energy obtained by the shape of the throat are not utilized effectively. Further, the introduction of the hydrocarbon feedstock is in the axial direction of the reactor, whereby the introduced hydrocarbon feedstock is obliged to diffuse in the radial direction of the reactor, and it is impossible to introduce the hydrocarbon feedstock swiftly and collectively to the area where the turbulent flow energy is maximum. Accordingly, the control to obtain a carbon black having optional desired properties, is very difficult, and it is particularly difficult to produce carbon black having a small particle size.

Further, in Japanese Examined Patent Publication No. 10581/1987, a plurality of carbon black intermediate gas streams formed separately, are collided with each other. However, the collision in this case is collision of carbon black intermediate gas streams themselves after introduction of a hydrocarbon feedstock, and the turbulent flow energy by the collision does not serve for efficient formation of carbon black. Further, the convergence of carbon black intermediate gas streams is conducted by an assembly of at least two first and second reaction zones, and it is likely that the carbon black intermediate products have already formed before the assembly. Consequently, the physical properties (quality) of the carbon black product tend to substantially vary. Further, if the number of series for the assembly increases, an increase of the surface area of the main body of the reactor is unavoidable, whereby the heat loss from the surface of the reactor increases, and the energy efficiency decreases.

B. Delivery of Carbon Black Suspensions

U.S. Pat. No. 5,401,242 relates to the delivery of substances, into the skin, particularly substances such as drugs, vaccines, biologicals and the like. Single needle syringes are used for this purpose, however, such devices are limited in their utility when it is desired to deliver medical substances into a relatively large area on the skin. In addition there is little control of these devices.

Another device which has great utility for injecting substances into the skin is a tattooing machine. Such an apparatus, particularly a tattooing machine embodying the present invention, would be useful for the known application of injecting pigment into the skin but it would be particularly usefull for injecting medical substances into the skin.

In the past, tattooing apparatus used needles comprising solid metal pins or solid metal points on pins for performing the injecting function. Usually several such solid pins were soldered together and they were used by being dipped periodically into the medication or pigment to be injected. In this procedure, capillary action causes the medication or pigment to be drawn up along the needles and sufficient material cannot always be readily provided in this way for good results.

C. Size

Carbon particles in carbon dye are heterogeneous and range from about 0.1 to about 6.0 microns in diameter. Filtered sulfur colloid particles used with a 99m-technetium label for radioisotopic localization of the sentinel node are less than about 0.2 microns in size, since a 0.2-micron filter is used in their preparation. Prefered diameters of carbon black particles is from about 0.2 to about 5.0 microns, or about 0.2 to about 4.0 microns, or about 0.2 to about 3.0 microns, or about 0.2 to about 2.0 microns, or about 0.2 to about 1.0 microns, or about 0.3 to about 1.0 microns, or about 0.3 to about 0.8 microns, or about 0.4 to about 0.7 microns.

D. Suspension Percentages

An example of a commercially available carbon dye (#4415, Sanford Corp., Belwood, Ill.) contains water (about 85%), carbon black (about 6%), and a suspending vehicle. Preferred concentrations of carbon black range from about 0.1% to about 6.0%, or from about 0.1% to about 5.0%, or from about 0.1% to about 4.0%, or from about 0.1% to about 3.0%, or from about 0.1% to about 2.0%, or from about 0.1% to about 1.0%, or from about 0.15% to about 1.0%, or from about 0.2% to about 1.0%, or from about 0.3% to about 1.0%, or from about 0.4% to about 1.0%, or from about 0.5% to about 1.0%. Evidence was found of carbon particles in sentinel nodes mapped with carbon concentrations as low as about 0.15%. In clinical practice, use of this concentration, with subsequent removal of stained lymph nodes and wide excision of the injection site, should minimize the risk for complication. It is possible a higher concentration may be required due to the relatively larger volume of lymphatic tissue in humans. The fact that carbon dye left a permanent mark at the primary injection site may limit its use to procedures requiring excision of the injection site. However, the carbon dye's mean radius of dermal diffusion was less than half that of isosulfan blue dye.

V. Carbon Particles in Combination with Other Methods

The present invention can be used in combination with a number of other techniques designed to image, detect, identify, stage, and diagnose cancer and metastasis. Current techniques include the use of dyes, radionucleotide tracers and other markers. This section outlines these current techniques as well as there associated detection systems.

In general, the present invention can be used with any existing diagnostic aid. Examples include Aminohippurate Sodium; Anazolene Sodium; Arclofenin; Arginine; Bentiromide; Benzylpenicilloyl Polylysine; Butedronate Tetrasodium; Butilfenin; Coccidioidin; Corticorelin Ovine Triflutate; Corticotropin, Repository; Corticotropin Zinc Hydroxide; Diatrizoate Meglumine; Diatrizoate Sodium; Diatrizoic Acid; Diphtheria Toxin for Schick Test; Disofenin; Edrophonium Chloride; Ethiodized Oil; Etifenin; Exametazime; Ferristenc; Ferumoxides; Fenunoxsil; Fluorescein; Fluorescein Sodium; Gadobenate Dimeglumine; Gadoteridol; Gadodiarnide; Gadopentetate Dimegiumine; Gadoversetamide; Histoplasmin; Impromidine Hydrochloride; Indigotindisulfonate Sodium; Indocyanine Green; $^{123}$I lobenguane Sulfate; Iobenzamic Acid; Iocarmate Meglumine; Iocarmic Acid; Iocetamic Acid; Iodarnide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopanoic Acid; Iopentol; Iophendylate; Iprofenin; Iopronic Acid; Ioprocemic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxaglate Meglumine; Ioxagiate Sodium; Ioxaglic Acid; Ioxilan; Ioxotrizoic Acid; Ipodate Calcium; Ipodate Sodium; Isosulfan Blue; Leukocyte Typing Serum; Lidofenin; Mebrofenin; Meglumine; Metrizamide; Metrizoate Sodium; Metyrapone; Metyrapone Tartrate; Mumps Skin Test Antigen; Pentetic Acid; Propyliodone; Quinaldine Blue; Schick Test Control; Sermorelin Acetate; $^{123}$I Sodium Iodide; Sprodianide; Stannous Pyrophosphate; Stannous Sulfur Colloid; Succimer; Teriparatide Acetate; Tetrofosmin; Tolbutamide Sodium; Tuberculin; Tyropanoate Sodium; Xylose.

A. Dyes

Optical imaging with dyes permit visualization of biological activities (Blasdel et al., 1986; Grinvaldet al., 1988; Kauer et al.,1988; Lieke et al., 1989). Dyes that are sensitive to physicochemical environments (such as pressure, cell membrane potential, ion concentration, acidity, partial pressure of oxygen, etc.), are subject to changes in absorption or emission of light. The resulting changes act as optical probes to transform biological activities into optical signals that can be converted into optical images.

Water soluble dyes are particularly well-suited, including acid dyes, basic dyes, direct dyes, and so on, and equivalents thereof. The dye composition may be prepared as a dry material for ease of storage and packaging. If prepared as a dry composition, prior to usage the composition may be prepared as a solution using a suitable liquid, including water and various organic solvents, or mixtures thereof and so on, by techniques well known to those skilled in the art. It is particularly preferred that compatible dyes are used, with a particularly preferred embodiment utilizing anionic dyes. Although the method of formulating may be accomplished using various amounts of dyes, a particularly preferred composition employs a total dye concentration of from about 0.1 to about 10 mM. Further, the stability of the reference materials will be increased when high purity dyes, which are either commercially available or purified, using conventional methods known to those skilled in the art, are used in formulation.

Several dyes exist that can be used in combination with carbon black suspensions for visualization of lymph nodes. These include Tartrazine (CI 19140), Quinoline Yellow (CI 47005), Eosin (CI 45380), Acid Phloxine (CI 45410), Erythrosine (CI 45430), Sunset Yellow FCF (CI 15985), Acid Violet 5B (CI 42640), Patent Blue AF (CI 42080), Brilliant Cyanine 6B (CI 42660), Acid Brilliant Blue FCF (CI 42090), Naphthalene Green VSC (CI 44025) and Acid Blue Black 10B (CI 20470); and direct dyes such as Paper Yellow GG (CI Direct Yellow 131), Direct Scarlet 4BS (CI 29160), Congo Red (CI 22120), Violet BB (CI 27905), Direct Sky Blue 5B (CI 24400), Pentamine, Phthalocyanine Blue (CI 74180), Black G (CI 35255) and Deep Black XA (CI Direct Black 154). The CI number in the description above indicates the identification number in the Color Index, 3rd Ed., The Society of Dyers and Colorists, Bradford, Yorkshire (1971). Prefered dyes include Isosulfan blue (Patent Blue Violet, Sulfan Dye), Direct Sky Blue, Pentamine, guajazulen blue or other dye which travels through the lymphatic system.

B. Radionucleotide Tracer

Several methodologies for methods and compositions for imaging, detecting and other lymphographic techniques are known to those of skill in the art. U.S. Pat. Nos. 5,776,095, U.S. Pat. No. 5,776,094, U.S. Pat. No. 5,776,093, U.S. Pat. No. 5,728,369, and U.S. Pat. No. 4,735,210 are examples and are herein incorporated by reference.

It has been shown in the examination of lymphatic drainage of melanoma, and now shown in the lyrnphatic drainage of breast cancers, that lymphatic drainage patterns can be defined by the injection of a radioisotope (or other traceable marker such as blue dye) into the bed of the tumor. The isotope (or dye) is then followed, either visually, with a gamma camera imaging system, or with a Geiger counter-type of counting system. Examples of radionucleotide tracers include technetium labeled sulfer or albumin colloid, antimony chloride, or other colloidal radionucleotide that travels through the lymphatic system.

The spread of cancer cells is orderly, the first lymph node reached by the drainage channels from the infected breast containing the most cancer cells. Consequently, the first lymph node in the draining system is referred to as the "sentinel" lymph node.

It has been further shown, if one simply removes the sentinel lymph node, the determination of whether or not breast cancer has metastasized to the regional lymph nodes of the axilla can be established without excision of the remaining lymph nodes in the axilla. The surgical removal of only one lymph node greatly reduces the complications of lymph node surgery including the morbidity of lymph edema.

The elements of a percutaneous sentinel lymph node biopsy are as follows: The tumor site in the breast is injected with a radioisotope (such as technicium 99 m labeled sulfur colloid) which travels via the lymphatic channels to the sentinel lymph node. The sentinel lymph node then becomes radioactively visible, or "hot." Radionucleotide detectors are able to identify or locate the radioactive lymph node through auditory and other signals, indicating when the apparatus is adjacent to the sentinel lymph node. The detectors is further able to then characterize or "visualize" the surrounding tissue with the associated ultrasound portion of the apparatus. It is important to identify the associated structures adjacent to the lymph node, because relatively large blood vessels (arteries, veins,) and nerves traverse the axilla. With the combination of percutaneous Geiger counter identification and percutaneous ultrasound identification, the sentinel lymph node can be identified and biopsied without entering a major blood vessel or severing a major nerve.

With respect to the radiolabel of choice, the ability to use a radiation detection probe that can be placed in immediate adjacency to the lymph node means that lower level energy isotopes are preferred, especially those exhibiting photon emissions of energy levels less than about 300 kev advantageously and preferably less than about 150 kev. $^{125}$I currently is the isotope of choice, although additional low energy isotopes, as disclosed in U.S. Pat. No. 4,782,840 patent, may be used as is necessary, desirable, or convenient. Higher energy level radioisotopes (e.g. $^{131}$I) also may be used, although suitable collimation of the radiation detection probe must be employed, which may impede the instrument being facile to the surgeon and limit the areas within the body cavity which can be suitably surveyed. $^{125}$I is preferred because it produces very low energy radiation and optimizes tumor contrast. Also, laparoscopic surgery can only be completed successfully with $^{125}$I.

In addition to radioisotopes emitting gamma radiation, radioisotopes exhibiting beta radiation additionally can be used in conjunction with a probe which can detect beta radiation or positrons. The detection of beta radiation intraoperatively is disclosed, for example, in U.S. Pat. No. 5,008,546, the disclosure of which is expressly incorporated herein by reference.

C. Other Reagents

A variety of radiopharmaceuticals have been evaluated for diagnostic imaging. For example, Michelot et al. (1991), Meyniel et al. (1990) and French Patent Publication 2,642, 972 by Morean et al. have disclose $^{123}$I and $^{125}$I N-(diethylaminoethyl)4-iodobenzamide (i.e. IDAB) for imaging malignant melanoma in humans. Unfortunately, the synthesis of IDAB is problematic and, more significantly, IDAB is taken up in high concentrations by non-melanoma cells in the liver and lung. Accordingly, IDAB does not have optimal specificity for melanoma cells and its uptake by non-tumor cells undermines its utility for routine screening of cancer.

U.S. Pat. No. 4,279,887 to Baldwin et al., U.S. Pat. No. 5,154,913 to De Paulis et al. and Murphy et al. (1990) disclose radioiodonated benzamide compounds for use in imaging the brain only, e.g. $^{123}$I-N-β-phenethyl-o-iodobenzamide or (S)-N→(1-ethyl-2-pyrrolidinyl)methyl-2-hydroxy-3-iodo-6-methoxybenzamide (IBZM).

U.S. Pat. No. 5,911,970 descibes compounds which bind with high specificity and affinity to the cell surface of cancer cells. These compounds bind, for example, to receptors on the cancer cell surface. One such receptor is a sigma receptor. Sigma receptors are known to be present on neural tissues and certain immortalized neuroblastoma and glioma cell lines (Walker et al., 1990; Villner et al., 1992). However, it has been surprisingly found that sigma receptors are prevalent on some types of cancer cells, e.g. neuroblastoma, melanoma, glioma, pheochromocytoma, colon, renal and lung carcinoma cells. Recently, John et al. (1994) have found that MCF-7 breast tumor cells express sigma receptors. Therefore the compounds of the present invention are useful for detecting and treating tumors, e.g. those containing cells with sigma receptors.

Other reagents useful for identification of cancer cells and associated metastasis include any substance which preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778) and like substances have been developed and may similarly prove efficacious. Biochemistry and genetic engineering may yet produce substances which mimic the function of antibodies in selectively concentrating at the sites of neoplastic tissue (perhaps, even hormones, peptides and other proteins, or the like), though such substances may not be subsumed within the traditional definition of "antibody". "Locator" was chosen as the term to include present-day antibodies and equivalents thereof, as well as those substances yet to be determined which mimic antibodies in the inventive method disclosed herein.

D. Detectors

With respect to the detection of lymph node sites exhibiting accretion of the radiolabeled locator, reference is made to the following patents which show a preferred hand-held probe for the detection of gamma radiation: U.S. Pat. Nos. 4,801,803, 4,889,991, and 5,070,878, the disclosures of which are expressly incorporated herein by reference. As stated above, U.S. Pat. No. 5,008,546 discloses a probe suitable for the detection of beta radiation. Additional radiation detection devices can be used as is necessary, desirable, or convenient. In this regard, it will be appreciated that intraoperative accessing of the patient in order to determine lymph node involvement is but one alternative for practice of the present invention. Additionally, probes may be used as part of an laproscope, mediastinoscope, or like specific instrument which suitably can be outfitted with a miniaturized radiation detection device which can be placed in immediate adjacency with the lymph node in order to determine accretion of radioactivity. Regardless of the instrument or technique employed, the present invention encompasses all such instruments and techniques, by whatever label.

Lymph node identification and mapping in association with radionucleotide tracers make use of detectors for the tracer. U.S. Pat. No. 4,782,840 by Martin and Thurston, entitled "Method for Locating, Differentiating, and Removing Neoplasms," reviews the approaches of nuclear medicine for locating colonic tumor using a hand held radiation responsive probe. The patent discloses a method for locating, differentiating, and removing neoplasms which utilizes a radiolabelled antibody in conjunction with the radiation detection probe, which the surgeon may use intraoperatively in order to detect the sites of radioactivity. Because of the proximity of the detection probe to the labelled antibody, the faint radiation emanating from occult sites becomes detectable because, in part, of the inherent application of the approximate inverse square law of radiation propagation. The procedure is known as the RIGS (Radioimrnuno-guided surgery) procedure. The RIGS system has been found to provide a unique identification of involved lymph nodes for staging evaluation (Nieroda et al., 1989). This RIGS lymph evaluation also may be employed with certain more minimally invasive procedures as described by Arnold and Thurston, in U.S. Pat. No. 5,383,456, entitled "Radiation-Based Laparoscopic Method for Determining Treatment Modality."

As an aspect of the RIGS system, the location of involved lymph material or neoplasm is carried out utilizing a statistical approach. With this approach, a background count rate of radiation emanation is developed, for example, at the aorta of the patient for an interval of time, for example, 5 seconds. A microprocessor-based control system then calculates a statistically significant value, for example a predetermined number of standard deviations of the basic count rate to derive a statistically significant threshold radiation count rate level. The ranging procedure is referred to by surgeons as "squelching." Operating in conjunction with that threshold level, the instrument provides the surgeon with audible cues representing that a high probability of tumor involvement is present at a location closely adjacent the forward window of the hand-held probe.

Radionucleotide tracers allow the mapping or surveying of a lymph vessel which drains from the site of a neoplasm such as a melanoma or breast tumor to a sentinel lymph node. They also aid in the detection and isolation of that node once its regional position is located. In general, the phenomenon associated with radiation propagation or photon emission is somewhat different when considering radiation emanating from a lymph duct as opposed to radiation emanating from a small source such as a lymph node. Equipment which is utilized in carrying out the diagnostic modality preferably is an adaptation of the equipment heretofore employed with the radioinrnuno-guided surgical system (RIGS) or procedure used in the location of tumor sites, for example, in the colonic region. The RIGS procedure typically is employed with a radiolabelled locator which specifically binds a marker produced or associated with neoplastic tissue. Such locators include substances which preferentially concentrate at tumor sites by binding with a marker (the cancer cell or product of the cancer, for example) produced by or associated with neoplastic tissue or neoplasms. Because the locater is injected into the bloodstream of the patient, equipment used with the RIGS procedure necessarily must work with radiation background levels and low radionuclide concentrations at tumor sites. For example, a sulfur colloid labeled with $^{99m}$Tc may be used, it being of relatively low cost, readily available, and representing an approved pharmaceutical product. Another advantage associated with its use resides in its short halflife (6 hours) which results in its being essentially gone from the body of a patient in about three days following injection. It exhibits a higher energy (140 Kev) than the materials employed with the RIGS system, however, this is not a significant characteristic, lower energy radionuclides having been used successfully.

The RIGS system is one wherein a hand-held radiation detecting probe is provided which preferably supports a cadmium zinc telluride detector or crystal of sufficient surface area to detect the minute levels of radiation involved in that procedure. Such a detecting probe is described, for example, in U.S. Pat. No. 5,070,878. As the probe is held by the surgeon, the window component thereof at its tip is moved along tissue being evaluated. During this surveying maneuver, as radiation is encountered, it is first evaluated for appropriate energy levels, and then statistically evaluated in terms of count rates. Where a statistically significant count rate is encountered, the probe is operated in an aural or sound mode manifested as a siren sounding to alert the surgeon. The noted statistical analysis of count rate is generally based upon a number of standard deviations above a base count rate. That computed level is referred to as a squelch threshold count rate value. The base count rate is developed by holding the crystal face of the probe against, for example, a region of the heart for an interval of five seconds to then generate an average count rate for that interval. Then, the software algorithm of the associated control unit, depending upon its operational mode, will establish the presence of tumor, for example, at a level of three standard deviations (three sigma) above the base count rate. This algorithm is described, for example, in U.S. Pat. No. 4,889,991, entitled "Gamma Radiation Detector with Enhanced Signal Treatment," and assigned in common herewith which is incorporated herein by reference.

The dosage of labeled locator is such that the radiation detection probe can be utilized for determining lymph node sites exhibiting accretion of the radiolabeled locator. Such dosages depend upon the specific type of label, the type of locator, and like factors which may affect dosage requirements as those skilled in the art will appreciate.

VI. Administration and Delivery Routes

According to the present invention, one may administer the carbon black suspension to a patient by direct injection of a tumor, its vasculature, or surrounding lymphatic system. Alternatively, the tumor may be infused or perfused with the carbon black suspension compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 minutes, to about 2–6 minutes, to about 6–12 minutes, to about 12–24 minutes, to about 1–2 hours, to about 2 to 4 hours or longer following the initiation of treatment.

An exemplary course of administration, for a primary tumor or a post-excision tumor bed, could involve multiple doses. Various combinations of carbon black suspension and dyes and/or radionucleotide tracers may be employed, either used sequentially or simultaneously. For instance, where carbon black suspension is "A" and the dye and/or radionucleotide tracer is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/B/A |
| B/A/B/A | B/A/A/B | A/A/A/B | B/A/A/A | A/B/A/A | A/A/B/A |

The time between treatment of dyes and/or radionucleotide tracers and carbon black suspension may be for a period from about 1–2 minutes, to about 2–6 minutes, to about 6–12 minutes, to about 12–24 minutes, to about 1–2 hours, to about 2 to 4 hours or longer following the initiation of treatment. Alternatively, simultaneous administration of carbon black suspension and dyes and/or radionucleotide tracers, with or without sequential administration of either carbon black suspension or dyes and/or radionucleotide tracers could also be employed.

Preferably, time is permitted to elapse following administration of the carbon black suspension with or without the associated indicator in order for unbound indicator to be cleared from the tissue surrounding the lymph nodes to be surveyed. Suitable indicator detection probes function by determining a level of indicator over and above that normal background found at the location (e.g., operating room) where the patient is being surveyed as well as the blood pool background (indicator circulating in the blood stream), and surrounding tissue which may contain circulating unbound indicator. The time may be as short as a few minutes on up to several weeks, depending upon how fast the patient's body clears (often metabolizes) the radiolabeled locator. Of importance is the recognition that the indicator will be associated with the tumor cell, albeit at reduced levels, after such time period has elapsed. Importantly, it is inappropriate to survey the lymph nodes based upon maximum tumor uptake of the indicator as is traditionally taught in external scintigraphy and external imaging technology.

Once the suitable interval has elapsed, the patient is accessed with the detection probe and lymph node sites are surveyed for carbon black accumulation.

The diagnostic compositions are administered in doses effective to achieve the desired enhancement. Such doses may vary widely, depending upon the particular dye employed, the organs or tissues which are the subject of the imaging procedure, the imaging procedure, the imaging equipment being used, and the like.

Aqueous compositions of the present invention comprise an effective amount of the carbon black suspension, further dispersed in pharmaceutically acceptable carrier or aqueous medium. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the compositions is contemplated. Supplementary active ingredients also can be incorporated into the compositions.

Solutions of compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antioxidants, chelating agents and inert gases. The pH and exact concentration of the various components the pharmaceutical composition are adjusted according to well known parameters.

The compositions of the present invention may include classic pharmaceutical preparations. Administration of therapeutic compositions according to the present invention will be via any common route so long as the target tissue is available via that route. This includes oral, nasal, buccal, rectal or vaginal. Alternatively, administration will be by orthotopic, intraderrnal subcutaneous, intramuscular or intraperitoneal injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Carbon Particle Dye in Animal Lymph Node Diagnostics

An animal model was used to demonstrate that intraoperative LM/SL using an injection of carbon dye at the primary site as an adjunct to isosulfan blue results in identifiable carbon particles in sentinel nodes on permanent section examination.

Animals

Twenty-two adult Sprague-Dawley rats weighing 300–500 g were obtained after receiving approval from the Animal Care and Use Committee at the Harbor-UCLA Research and Education Institute. All animals were obtained at least one day prior to planned procedures.

Contrast Agents

Isosulfan blue dye (Lymphazurin 1%) was obtained from Hirsch Industries, Inc. (Richmond, Va.). Carbon dye containing 6% carbon black (# 4415) was obtained from Sanford Corporation (Bellwood, Ill.) and either used alone at full strength or mixed with isosulfan blue and/or sterile normal saline in the concentrations shown in Table 1.

TABLE 1

Mixtures of carbon dye, isosulfan blue dye, and saline solution for intraoperative lymphatic mapping

| Composition | Carbon Concentration |
| --- | --- |
| 50% carbon dye + 50% isosulfan blue dye | 3% |
| 10% carbon dye + 90% isosulfan blue dye | 0.6% |
| 10% carbon dye + 90% saline solution | 0.6% |
| 2.5% carbon dye + 97.5% saline solution | 0.15% |
| 2.5% carbon dye + 7.5% saline solution + 90% isosulfan blue dye | 0.15% |

All mapping solutions containing ink were sterilized in an autoclave at 121° C. for 25 m, prior to injection.

Sentinel Lymph Node Dissection

All procedures were performed under general anesthesia. Rats were anesthetized with a mixture of ketamine (42.9 mg/kg), xylazine (8.6 mg/kg), and acepromazine (1.4 mg/kg). A half-dose of this mixture was readministered at 60 minutes and then every 30 minutes. Buprenorphine (0.01–0.05 mg/kg) was administered subcutaneously for postoperative analgesia.

The inguinal regions of the animals were shaved. A 29-gauge needle with a 1-cc tuberculin syringe was used to inject 0.04 cc of the mapping solution intradermally just below the medial aspect of the knee on the lower extremity. Five minutes later, and under sterile conditions, an incision was made over the region of the inguinal lymph nodes. The inferior skin flap was elevated and the lymphatic channel identified. The lymphatic was followed to the first stained lymph node. Further dissection was carried out to identify additional stained nodes. All stained nodes were removed and placed in formalin. Nonstained nodes in the same drainage basin were removed and fixed in a similar fashion, and analyzed for carbon particles. The identical procedure was performed on the contralateral extremity of each animal using an alternative mapping mixture.

Wounds were closed with 4-0 polyglactin 910 (Vicryl) sutures, and animals were observed for at least 28 days. Blood samples were obtained from all animals prior to euthanasia, and were analyzed for complete blood cell count, alanine aminotransferase, albumin, total protein, serum urea nitrogen, creatinine, and glucose.

Histologic Evaluation

Lymph nodes were placed in paraffin blocks, serially sectioned, and stained with hematoxylin and eosin (H and E). Each lymph node was evaluated by light microscopy for the presence of carbon particles.

Results

Full-Strength Carbon Dye Versus Isosulfan Blue Dye

Six animals received full-strength carbon dye in one extremity and isosulfan blue dye in the other extremity. Following injection of carbon dye, afferent lymphatic channels were identified and followed to a stained node in all 6 basins. All stained nodes were a deep blue-black color. Five basins contained a single stained node, and one basin had two stained nodes. Although carbon particles were identified in all 7 stained nodes, their large number obscured histologic detail. None of the 4 nonstained nodes excised from the same basins contained carbon particles.

Isosulfan blue dye stained a lymphatic channel and a draining lymph node (the sentinel node) in all 6 contralateral basins. Sentinel nodes were bright blue. Four basins had a solitary sentinel node and 2 basins each had 2 sentinel nodes (total of 8 sentinel nodes). Two nonsentinel nodes were pathologically unremarkable.

50% Carbon Dye/50% Isosulfan Blue Dye Versus Isosulfan Blue Dye

Four animals received a 50:50 mixture of carbon dye and isosulfan blue dye in one extremity and isosulfan blue dye in the other extremity. The afferent lymphatic and a single stained sentinel node were found in all 4 basins mapped with the carbon dye/blue dye mixture. These nodes were predominantly blue, with black tinting at the pole into which the afferent lymphatic drained. Although the 50:50 mixture of carbon dye and blue dye deposited fewer carbon particles in the nodes, the clumping of these particles hampered visualization of histologic detail. None of the nonsentinel nodes (n=2) contained carbon.

Isosulfan blue effectively identified the lymphatic channel and sentinel node(s) in the paired extremities. One basin had 2 sentinel nodes.

10% Carbon Dye/90% Normal Saline Versus 10% Carbon Dyel90% Isosulfan Blue Dye

Four animals received carbon dye diluted 10:90 with normal saline in one extremity and a 10:90 mixture of carbon dye/isosulfan blue dye in the other extremity. There was no difference in time from injection of agents to identification of afferent lymphatic and sentinel node (5 min). A solitary sentinel node was identified in each of the 8 basins. Carbon particles were identified in all 8 sentinel nodes but in none of the 4 nonsentinel nodes.

Nodes stained with the carbon dye/saline mixture were light brown-black in color. Histologic detail was not obscured at this concentration of carbon (0.6%). The carbon dye/blue dye mixture produced a bright blue coloration that on gross visual inspection was indistinguishable from that produced by pure isosulfan blue.

2.5% Carbon Dye/97.5% Saline versus Isosulfan Blue Dye

Two animals received a 2.5:97.5 mixture of carbon dye and saline (0.15% carbon) in one extremity and blue dye alone in the other extremity. Five minutes after injection of the carbon/saline mixture, neither the lymphatic channel nor the sentinel node could be identified in one animal, and one lightly stained sentinel node (brownish-gray) was identified in the second animal. This node contained carbon particles on light microscopy. No nonsentinel nodes were identified. Isosulfan blue clearly identified one sentinel node in each paired basin (n=2).

2.5% Carbon Dye/7.5% Saline/90% Isosulfan Blue Dye

Six animals underwent mapping with a 2.5:7.5:90 mixture of carbon dye, saline, and blue dye in both extremities. Lymphatic channels and sentinel nodes were identified in all 12 basins. One basin had 2 stained nodes. Nodes were a bright blue color that was not readily discernible from that produced by pure isosulfan blue. Carbon particles were identified in all 13 sentinel nodes but in none of the 6 nonsentinel nodes. Histologic detail was not obscured by carbon at this concentration.

Dermal Diffusion

Carbon dye exhibited significantly less dermal diffusion than did isosulfan blue dye. Mean radius of diffusion was 1.5 mm for full-strength carbon dye and 6.0 mm for isosulfan blue dye. However, carbon staining of skin was permanent, whereas blue staining faded at variable rates over the observation period.

Toxicity

No toxicity was apparent on inspection of the animals throughout the observation period. No laboratory abnormalities were identified, except in 2 rats that had mildly elevated lymphocyte counts but normal white blood cell counts.

Discussion

Carbon dye has been used for many years to produce the black color of traditional tattoos. In medicine, it serves as both a diagnostic and therapeutic agent. Carbon dye is used to mark polypectomy sites within the colon to facilitate endoscopic surveillance (Ponsky and King, 1975; Botoman et al., 1994), and to designate port sites for direction of the radiation beam. Carbon particle suspensions have been used to delineate early colon cancers to facilitate laparoscopic colectomy (Kitamura et al., 1995), and to identify lymph node drainage patterns in gastric (Kodama and Koyama, 1991; Kitamura et al., 1995) and pancreatic (Nagakawa et al., 1994) carcinomas. Cytotoxic drugs have been adsorbed to activated carbon particles, in an attempt to distribute greater amounts of these agents into lymph nodes (Hagiwara et al., 1986; Takahashi et al., 1991).

Several studies have documented the safety of carbon dye in clinical use. Hyman and Waye (1991) reported no complications or toxicity in 40 patients receiving an injection of 0.4 to 1.0 ml full-strength carbon dye for endoscopic tattooing. Fennerty et al. (1992) prospectively studied 26 patients who had 32 carbon dye tattoos implanted within the colonic mucosa using a sterilized 10% ink solution. There were no side effects from ink injection and no local complications. Mean follow-up was 14 months. Endoscopic biopsy of the injection site at 3 months revealed carbon particles without any associated inflammatory reactions. Maruyama et al. (1989) reported no apparent adverse effects of intraperitoneal injection of carbon particle suspensions in over 3700 patients.

In an animal study, the intradermal injection of sterilized carbon dye produced no complications and no evidence of toxicity. Carbon dye contains water (85%), carbon black (6%), and a suspending vehicle. Evidence was found of carbon particles in sentinel nodes mapped with carbon concentrations as low as 0.15%. In clinical practice, use of this concentration, with subsequent removal of stained lymph nodes and wide excision of the injection site, should minimize the risk for complication. It is possible a higher concentration may be required due to the relatively larger volume of lymphatic tissue in humans. The fact that carbon dye left a permanent mark at the primary injection site may limit its use to procedures requiring excision of the injection site. However, the carbon dye's mean radius of dermal diffusion was less than half that of isosulfan blue dye.

These results suggest a role for carbon dye as an adjunct to isosulfan blue dye for intraoperative lymphatic mapping of the sentinel lymph node. Full-strength carbon dye (0.6% carbon) successfully identified sentinel lymph nodes in all basins studied, but at this concentration visualization of cancer cells in clinical practice could be hindered by carbon particle volume. Identification of sentinel nodes became difficult at a carbon concentration below 0.3%. Addition of isosulfan blue dye lowered this threshold to 0.15% carbon; the blue dye allowed intraoperative identification of the sentinel node, and the carbon particles provided histopathologic confirmation.

Carbon particles in carbon dye are heterogeneous and range from 0.1 to 6.0 microns in diameter. Filtered sulfur colloid particles used with a 99m-technetiun label for radioisotopic localization of the sentinel node are less than 0.2 microns in size, since a 0.2-micron filter is used in their preparation. In this rat model, it is possible that the carbon particles were phagocytosed by macrophages and carried into the first draining node(s) from the limb. Most of the carbon particles observed on light microscopic examination of lymph nodes were present within macrophages and were less than 1.0 micron in diameter. The black color of carbon particles was distinctly different from the brown color of melanin pigment. Phagocytosis of carbon particles up to 0.2 microns in diameter by macrophages, and subsequent transport into lymphatics has been reported previously (Brandwood et al., 1992).

Carbon was not identified in nonstained nodes, but identification of nonstained nodes in the rats was difficult, and the number of nonsentinel nodes examined was low. A feline model (Wong et al., 1991) would provide a larger number of groin nodes for examination, but approval of feline studies is difficult in this region, and study costs are significantly higher.

Harvesting of lymph nodes was usually completed within 30 m after injection of the carbon dye. It is difficult to ascertain from this study whether carbon particles travel beyond the first draining lymph node(s) when the time from injection to harvest is delayed significantly.

Combined use of radiolabeled sulfur colloid and isosulfan blue dye for intraoperative lymphatic mapping improves rates of successful nodal staging in melanoma patients (Kapteijn et al., 1997; Gershenwald et al., 1998). However, neither agent is visible on histopathologic examination, and both agents travel to successive nodes at variable rates. Nonstandardization of the radionucleotide tracer technique, including inconsistency in the definition of a sentinel node, remains a problem. Addition of carbon particles to the dye/colloid combination might not improve the intraoperative rate of sentinel node identification, but it can validate sentinel lymph node status at histopathologic examination.

Example 2

Carbon Dye Histopathologically Confirms Sentinel Node Removal in Cutaneous Melanoma Lymphatic mapping and sentinel lymphadenectomy (LM/SL) is associated with a low false negative rate related to technical failures in nuclear medicine and surgery or by erroneous histopathologic evaluation. The present example demonstrates that carbon dye compositions may be used histologically to verify sentinel nodes removed at LM/SL and may decrease the false negative rate.

Patients

Consecutive patients with American Joint Committee on Cancer (AJCC) Stage I and II melanoma who underwent LM/SL between January 1997 and April 2000 were enrolled in a protocol that was approved by the joint Saint John's Health Center and the John Wayne Cancer Institute Institutional Review Board at Santa Monica, Calif., and that complied with the ethical standards of the Helsinki Declaration. Written informed consent was obtained from all study participants.

During the study period, 100 consecutive patients with melanoma and clinically negative nodes were enrolled. Patient demographics and primary tumor features are shown in Table 2.

TABLE 2

Characteristics of Patient Population

| | |
|---|---|
| Age (median, range) | 56, 20–88 |
| Gender, % | |
| Male | 63 |
| Female | 37 |
| Site of primary melanoma, % | |
| Trunk | 44 |
| Extremity | 42 |
| Head and Neck | 14 |
| Breslow thickness | |
| Median, mm | 1.28 |
| Range, mm | 0.28–10 |
| <1 mm | 32 |
| 1–2 mm | 40 |
| 2–3 mm | 13 |
| 3–4 mm | 7 |
| >4 mm | 7 |
| Unknown | 1 |

Median age was 56 years. Breslow thickness ranged from 0.25 mm to 10 mm, with a median of 1.28 mm. Primary tumors were most often located in the trunk (44%) and extremity (42%), with a minority in the head and neck (14%).

LM/SL was performed using carbon dye (India ink) combined with isosulfan blue and sulfur colloid. Sentinel nodes, defined as blue/black or radioactive, and non-sentinel nodes removed at LM/SL or complete lymph node dissection (CLND) were evaluated for the presence of carbon particles. Only patients with tumor-positive sentinel nodes underwent CLND.

Preoperative Lymphoscintigraphy

Preoperative dynamic lymphoscintigraphy was performed with technetium-99m (Tc-99m) sulfur-colloid (Amersham-Medi-Physics, Arlington Heights, Ill.). The primary site was injected as previously described (Morton et al., 1992), and the skin overlying any sentinel nodes was marked by the nuclear medicine physician with an indelible marking pen.

Lymphoscintigraphy identified 117 lymph node drainage basins and drainage to sentinel nodes in the scapular area in 3 patients for a total of 120 drainage regions. Eighteen patients had more than one drainage region.

LM/SL

After general anesthesia was induced and the patient was suitably prepared, 1–1.5 cc of sterilized India ink (6% carbon black, # 4415, Sanford Corporation, Bellwood, Ill.) mixed with 1% isosulfan blue dye (Lymphazurin, US Surgical Corp, Norwalk, Conn.) in a ratio of 1:3 was injected intradermally around the primary melanoma. After about 5 min, an incision was made at the site marked at lymphoscintigraphy. The blue/black stained nodes as well as any radioactive nodes detected with a hand-held gamma probe (Neoprobe 1000 or 1500, Neoprobe Corp., Dublin, Ohio) were excised until the counts in the wound approached background levels. Background counts were obtained from a body site away from the primary injection site and lymph node basin, and an average was taken of three counts. Sentinel nodes were defined intraoperatively by the surgeon as either blue/black nodes, radioactive nodes with a node background ratio greater than two, or both blue/black and radioactive nodes. All other nodes removed were defined by the surgeon as non-sentinel nodes.

If sentinel nodes were positive for metastases either by frozen or permanent section, complete lymphadenectomy was recommended and performed in the standard fashion, unless the sentinel node was not located in a classic lymph node basin.

LM/SL was successful in all 100 patients. A total of 199 sentinel and 35 non-sentinel nodes were removed at the time of LM/SL. Eight sentinel nodes were only blue, 26 were only radioactive, and 165 were both blue and radioactive. The characteristics of blue/black or radioactive nodes in relation to the presence of carbon particles are presented in Table 3.

TABLE 3

Frequencies of Sentinel and Non-Sentinel Nodes Removed at LM/SL According to Blue/Black Color and/or Radioactivity

| | Carbon Present | Carbon Absent |
|---|---|---|
| | Number of Sentinel Nodes (%) | |
| Blue/Black +, Radioactive + | 147 (74) | 18 (9) |
| Blue/Black +, Radioactive − | 5 (2.5) | 3 (1.5) |
| Blue/Black −, Radioactive + | 11 (5.5) | 15 (7.5) |
| Total Blue/Black | 152 (76) | 21 (11) |
| Total Radioactive | 158 (79) | 33 (17) |
| Total Sentinel | 163 (82) | 36 (18) |
| | Non-sentinel Nodes | |
| Blue/Black −, Radioactive − | 1 (3) | 34 (97) |
| Total Non-sentinel | 1 (3) | 34 (97) |

'+' = present, '−' = absent

Mean node to background ratio was 117±608 for sentinel nodes and 0.97±1.1 for non-sentinel nodes.

A comparison of the color or radioactivity of sentinel nodes to the presence of carbon particles revealed blue/black sentinel nodes and tumor positive sentinel nodes is significantly correlated with the presence of carbon particles (Table 4).

TABLE 4

Comparison of Sentinel Node Status to the Presence or Absence of Carbon Particles

|  | Carbon + | Carbon − | Total | P-value |
|---|---|---|---|---|
| Blue/Black |  |  |  | P = 0.0001 |
| Positive | 152 | 21 | 173 |  |
| Negative | 11 | 15 | 26 |  |
| Radioactive |  |  |  | P = 0.159 |
| Positive | 158 | 33 | 191 |  |
| Negative | 5 | 3 | 8 |  |
| Histopathology |  |  |  | P = .028 |
| Positive | 20 | 0 | 20 |  |
| Negative | 143 | 36 | 179 |  |

The kinetics of India ink relate to the carbon particle size. Carbon particles in India ink are heterogeneous and range from 0.1 to 6.0 microns in diameter (Lucci et al., 1999). Most of the carbon particles on light microscopic examination of lymph nodes were approximately 1.0 micron in diameter, and were concentrated in macrophages within sentinel nodes. Filtered sulfur colloid particles labeled with Tc-99m are less than 0.2 microns in size. It is well known that with an increase in time, more nodes become radioactive because the smaller particle radiocolloids disperse to more than the first node encountered in a drainage basin (Glass et al., 1998). In this study, radioactive sentinel nodes removed at LM/SL did not correlate with the presence of carbon particles; rather, many radioactive nodes were often without carbon particles. Similarly, 1% isosulfan blue, a non-particulate dye, travels beyond the sentinel nodes with time, as does CH-40, a small carbon particle suspension (Yokota et al., 2000). The India ink used has larger particles, and it remained more localized than the radiocolloid. Interestingly, a few non-sentinel nodes from the CLND specimen contained carbon particles, but these were always accompanied by metastases. Blue/black nodes correlated with carbon particles, providing further evidence that blue/black nodes, particularly those with carbon particles, should now be considered true sentinel nodes.

Pathology

Gross and Histologic Sections

Each sentinel node was measured by the pathologist and depending on its size was bisected or sectioned longitudinally so that a tissue slice was no thicker than approximately 2 mm. Frozen sections were cut at one or two levels for intraoperative consultation by the pathologist. The remainder of the sentinel node was fixed in formalin, processed overnight, and embedded in paraffin. Paraffin sections were cut at two levels, separated by 40 $\mu$m, and examined with hematoxylin-eosin (H-E) staining and with S-100 protein and HMB-45 immunohistochemistry (IHC) on adjacent 4um tissue sections at each level. Diagnostic evaluation was performed by one of five rotating pathologists. These original slides of sentinel nodes were reviewed by the study pathologist (R. R. T). The non-sentinel nodes in patients that had tumor-positive sentinel nodes when available were examined for carbon dye and metastases after routine processing.

Carbon particles were identified in at least one sentinel node in 92 patients from the original slider; subsequent step sections of the original blocks identified 4 additional patients for a total of 96 patients with identifiable carbon particles (Table 5).

TABLE 5

Sentinel Node Tumor Status in 100 Patients and 120 Lymph Node Regions in Relation to the Presence or Absence of Carbon Particles

|  | Carbon Present | Carbon Absent |
|---|---|---|
| Patients |  |  |
| Tumor Positive | 16 | 0 |
| Tumor Negative | 80 | 4 |
| Lymph Node Regions |  |  |
| Tumor Positive Sentinel Nodes | 18 | 0 |
| Tumor Negative Sentinel Nodes | 93 | 9 |

No carbon particles were identified in the sentinel nodes of 4 patients, all of whom had tumor-free sentinel nodes. No previously undiagnosed metastases were identified in these additional step sections. Metastases were present in the sentinel nodes of 16 patients, and at least one sentinel node contained carbon particles in all of these patients.

Of the 199 sentinel nodes, 163 (82%) contained carbon particles, and all 20 tumor-positive sentinel nodes contained carbon particles. Of the 35 non-sentinel nodes removed during LM/SL, 34 (97%) did not contain carbon particles, and all were tumor-negative.

In the 16 patients with sentinel node metastases, one of these patients had a scapular sentinel node removed that did not reside in a lymph node basin, and another patient had a groin dissection at an outside institution with unavailable slides, leaving 14 patients whose non-sentinel nodes were evaluated in the complete lymph node dissection specimen. Of these 14 patients, 5 had micrometastases in only one non-sentinel node, and in 3 patients carbon particles accompanied the micrometastases. Two patients had micrometastases in non-sentinel nodes that were not accompanied by carbon particles. Interestingly, carbon particles were not found in any other non-sentinel nodes in the 14 patients.

Step Sections and IHC Techniques

All sentinel nodes negative for carbon dye were evaluated further by step sectioning the original sentinel node paraffin blocks at four additional levels with each level separated by 200 $\mu$m. At each level, adjacent 4 $\mu$m sections were prepared for H-E, S-100 protein and HMB-45 IHC stains. Tissue sections for IHC were placed on charged slides (Colorfast Plus, 12-550-17, Fisher Scientific, Pittsburgh, Pa.). A standard procedure employed an automated immunostainer (Ventana ES, Ventana Medical Systems, Inc., Tuscon, Ariz.) with polyclonal antibodies to S-100 protein (Dako Corporation, Carpenteria, Calif. 1:400 dilution, 32 min) and monoclonal antibody to HMB-45 (Dako, 1:100 dilution, 32 min). Further staining utilized the Ventana Basic detection kit with diaminobenzidine as chromogen. The slides were examined by the pathologist (R. R. T) for presence of carbon dye and micrometastases.

Follow-up

Patients were seen in follow-up within a week after surgery, and then were scheduled to be seen at 3, 6, and 12 months, and at 6 monthly intervals thereafter. Physical examination was performed at each visit. Any local or systemic complications were documented.

Median follow-up was 20 months. There were 17 patients who recurred; of these, 12 recurred only at distant sites, 3 recurred at both distant and same basin sites, and 2 recurred only in the same nodal basin. Therefore, 5 (5%) patients recurred in the same basin. Of these 5 same-basin recurrences, 4 had complete node dissections at initial surgery because of tumor-positive sentinel nodes, that also contained carbon particles. One patient who had tumor-negative sentinel nodes and carbon particles present recurred in the same basin after LM/SL only.

Ten patients died, and 9 were due to recurrent distant melanoma. One death was from an unknown cause. There was an overall complication rate of 6%. Three patients (3%) had wound infection or seroma of the sentinel node wound, and one patient had a seroma after axillary lymph node dissection. The wound at the site of wide excision dehisced in two patients (2%) after suture removal. No patients had lymphedema. No black tattooing was identified at the wide excision site. In 2 patients faint residual blue-stained skin was apparent.

Study patients showed no evidence of local or systemic adverse effects from the use of India ink. Carbon dye in the India ink preparation contained water, carbon black, and vehicle, and was well-tolerated. Carbon dye used for other clinical purposes has also been shown to be safe and non-toxic (Margevicius et al., 1996; Fennerty et al., 1992; Botoman et al., 1994; Eriguchi et al, 1991; Kitamura et al, 1995; Nagakawa et al., 1994). Furthermore, the indelible skin tattoo at the injection site is removed at the time of wide excision and is of no cosmetic consequence; the carbon dye actually remains more localized than isosulfan blue (Lucci el al., 1999). Any residual dermal staining is attributable to isosulfan blue.

Statistics

There were 100 patients enrolled who underwent successful LM/SL in 120 lymph node regions. Carbon particles were identified in sentinel nodes from 111 lymph node regions in 96 patients. Sixteen patients had tumor-positive sentinel nodes, and all contained carbon particles. There were 199 sentinel nodes and 35 non-sentinel nodes harvested during LM/SL. The Fisher's exact test was used to compare the presence of blue/black or radioactive sentinel nodes and their tumor status to the presence or absence of carbon particles. Statistical significance was determined using an $\alpha$-level of 0.05 and two-sided t-tests.

The presence of carbon particles correlated with blue/black sentinel nodes (p=0.0001) and with tumor-positive sentinel nodes (p=0.028), but not with radioactivity. All nonsentinal nodes from LM/SL were tumor-negative, and only one contained carbon particles. Five non-sentinel nodes from CLND contained metastases, and 3 were the only non-sentinel nodes that had carbon particles.

These results demonstrate that carbon particles were visualized in all sentinel nodes in patients with tumor-positive sentinel nodes. Metastases were found only in sentinel nodes that contained carbon particles. Thus, the present invention provides a method to identify sentinel nodes using composition comprising carbon particles, and this method of identification should alert the pathologist to scrutinize these true sentinel nodes for metastases.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Albertini et al., "Intraoperative radio-lympho-scintigraphy improves sentinel lymph node identification for patients with melanoma, *Ann. Surg.*, 223:217-224, 1996.

Albertini et al., "Lymphatic mapping and sentinel node biopsy in the patient with breast cancer," *JAMA*, 276:1818–1822, 1996.

Anderson et al.,. "Tattoo pigment mimicking metastatic malignant melanoma," *Dermatol Surg*, 22:92–94, 1996.

Bilchik et al., "Universal application of intraoperative lymphatic mapping and sentinel lymphadenectomy in solid neoplasms," *Cancer J*, 4:351–358, 1998.

Blasdel, G. G. and Salama, G. *Nature*, 321:579, 1986.

Bostick et al., "Comparison of blue dye probe-assisted intraoperative lymphatic mapping in melanoma to identify sentinel nodes in 100 lymphatic basins," *Arch Surg*, 134: 43–49, 1999.

Bostick et al., "Intraoperative lymphatic mapping for early-stage melanoma of the head and neck," *Am J Surg*, 174:536–539,1997.

Botoman et al., "Localization of colonic lesions with endoscopic tattoo," *Dis Colon Rectum*, 37:775–776, 1994.

Brandwood et al., "Phagocytosis of carbon particles by macrophages in vitro," *Biomaterials*, 13:646–648, 1992.

DeVita et al., "Cancer, Principles and Practice of Oncology", vol. 1, 4th ed. chapter 40, Harris, et al., J.P. Lippincott Co., Philadelphia, Pa., 1993.

Eriguchi et al., "Regional lymph node metastasis of early gastric cancer," *Eur J Surg*, 157:197–200, 1991.

Essner et al., "Efficacy of lymphatic mapping, sentinel lymphadenectomy, and selective complete lymph node dissection as a therapeutic procedure for early-stage melanoma," *Ann Surg Oncol*, 6A42–49, 1999.

Fennerty et al., "Effectiveness of India ink as a long-term colonic mucosal marker," *Am J Gastroenterol*, 87:79–81, 1992.

Gershenwald et al., "Patterns of recurrence following a negative sentinel lymph node biopsy in 243 patients with stage I or II melanoma," *J Clin Oncol*, 16:2253–2260, 1998.

Gershenwald et al., "Improved sentinel lymph node localization in patients with primary melanoma with the use of radiolabeled colloid," *Surgery*, 124:203–210, 1998.

Giuliano et al., "Sentinel lymphadenectomy in breast cancer," *J Clin Oncol*, 15:2345–2350, 1997

Glass et al., "Evaluation of in vivo kinetics of three lymphoscintigraphic agents in patients with cutaneous melanoma," *J Nucl Med*, 39: 1185–1190, 1998.

Grinvald et al., *Physiological Reviews*, 68:1285, 1988.

Guiliano et al., "Lymphatic Mapping and Sentinel Lymphadenectomy for Breast Cancer", *Annals of Surgery*, vol. 220, 3: 391–401, J. B. Lippincott Company, 1994.

Hagiwara et al., "Anticancer agents adsorbed by activated carbon particles, a new form of dosage enhancing efficacy on lymphnodal metastases," *Anticancer Res*, 6:1005–1008, 1986.

Hyman, N. and Waye, J. D. "Endoscopic four quadrant tattoo for the identification of colonic lesions at surgery," *Gastrointestinal Endoscopy*, 37:56–58, 1991.

John et al., *J. Med. Chem.* 37: 1737–1739, 1994

Joseph et al., "Radio-guided surgery for the ultra-staging of the patient with melanoma," *Cancer I Sci. Am.*, 3341–3345, 1997.

Kapteijn et al., "Localizing the sentinel node in cutaneous melanoma: gamma probe detection versus blue dye," *Ann Surg Oncol*, 4:156–160, 1997.

Kauer, J. S. *Nature*, 331:166, 1988.

Kelley et al., "Lymphatic mapping and sentinel lymphadenectomy for melanoma," *Semin Surg Oncol*, 14:283–290, 1998.

Kitamura et al., "Activated carbon-oriented gastrectomy for early gastric cancer," *Br J Surg*, 82:647–649, 1995.

Kitamura et al., "Rapid and accurate method for delineating cancer lesions in laparoscopic colectomy using activated carbon injection," *J Surg Oncol*, 58:31–33, 1995.

Kodama, M. and Koyarna, K. "Indications for pylorus preserving gastrectomy for early gastric cancer located in the middle third of the stomach," *World J Surg* 15:628–634, 1991.

Krag et al., "Minimal-access surgery for staging of malignant melanoma," *Arch Surg.*, 130:654–660, 1995.

Krag et al., "Surgical resection and radiolocalization of the sentinel node in breast cancer using gammna probe," *Surg Oncol*, 2:335–340, 1993.

Leong et al., "Optimal selective sentinel lymph node dissection in primary malignant melanoma," *Arch Surg*, 132:666–673, 1997.

Lieke et al., *Annu. Rev. Physiol.* 51:543, 1989.

Lingam et al., "Intraoperative identification of sentinel lymph node in patients with malignant melanoma," *Br J Cancer*, 75:1505–1508, 1997.

Loggie et al., "Prospective evaluation of selective lymph node biopsy for cutaneous malignant melanoma," *Am Surg*, 63:1051–1058, 1997.

Lucci et al., "Carbon dye as an adjunct to isosulfan blue dye for sentinel lymph node dissection," *Surgery*, 126:48–53, 1999.

Margevicius et al., "Identification and distribution of synthetic ligament wear particles in sheep," *J Biomed Mater Res*, 31:319–328, 1996.

Maruyama et al., "Reasonable lymph node dissection in radical gastrectomy for gastric cancer: introduction of computer information system and lymphography technique by India-ink," *Nippon Geka Gakkai Zasshi*, 90:1318–1321, 1989.

Meyniel et al. *C. R. Acad. Sci. Paris* 311:13–18, 1990.

Michelot et al., *J Nucl. Med.* 32:1573–1580, 1991.

Miliotes et al., "The tumor biology of melanoma nodal metastases," Am Surg, 62: 81–88, 1996.

Morton, D. L. and Bostick, P. J. "Will the true sentinel node please stand?" *Ann Surg Oncol*, 6:12–14, 1999.

Morton, D. L. and Chan, A. D. "Current status of intranperative lymphatic mapping and sentinel lyniphadenectotny for melanoma: is it standard of care?" *J Am Coll Surg*, 189:214–223, 1999.

Morton, D. L. "Intraoperative lymphatic mapping and sentinel lymphadenectomy: Community standard care or clinical investigation?" *Cancer J Sci. Am.*, 3:328–330, 1997.

Morton et al., "Intraoperative lymphatic mapping and selective lymphadenectomy: technical details of a new procedure for clinical stage I melanoma," Presented at the Society of Surgical Oncology, March 1990, Washington, D.C.

Morton et al., "Symposium: lymphatic mapping and sentinel node biopsy in patients with breast cancer and melanoma," *Contemp Surg*, 53:281–298 (part 1) and 53:353–361 (part 2), 1998.

Morton et al., "Intraoperative lymphatic mapping and selective cervical lymphadenectomy for early-stage melanomas of the head and neck," *J. Clin. Oncol.*, 11:1751–1756, 1993.

Morton et al., "Technical details of intraoperative lymphatic mapping for early stage melanoma," *Arch Surg*, 127:392–399, 1992.

Murphy et al., *J Med. Chem.* 33:171–178, 1990.

Nagakawa et al., "Clinical study of lymphatic flow to the paraaortic lymph nodes in carcinoma of the head of the pancreas," *Cancer*, 73:1155–1162, 1994.

Nieroda et al., *Surg. Gynecol Obstet.* 169(1):35–40, 1989.

Pijpers et al., "The impact of dynamic lymphoscintigraphy and gamma probe guidance on sentinel node biopsy in melanoma," *Eur. J. Nuc. Med.*, 22; 1238–1241, 1995.

Ponsky, J. L. and King, J. F. "Endoscopic marking of colonic lesions," *Gastrointestinal Endoscopy* 22:42–43, 1975.

Reintgen et al., "The orderly progression of melanoma nodal metastases," *Ann. Surg.*, 220:759–767, 1994.

Strom et al., "Retention and clearance of inhaled submicron carbon black particles," *J Toxicol Environ Health*, 26:183–202, 1989.

Sugarbaker, P. H. "Patterns of Metastasis in Human Malignancies", *Cancer Biol. Rev.*, 2:235, 1981.

Takahashi et al., "Type-oriented therapy for gastric cancer effective for lymph node metastasis: management of lymph node metastasis using activated carbon particles adsorbing an anticancer agent," *Semin Surg Oncol*, 7:378–383, 1991.

Thompson et al., "Sentinel lymph node status as an indicator of the presence of metastatic melanoma in regional lymph nodes," Melanoma Res., 5:255–260, 1995.

Thompson et al., "Single-dose isotope injection for both preoperative lymphoscintigraphy and intraoperative sentinel lymph node identification in melanoma patients, *Melanoma Res*, 7:500–506, 1997.

Uren et. al, "Lymphoscintigraphy in High-Risk Melanoma of the Trunk: Predicting Draining Node Groups, Defining Lymphatic Channels and Locating the Sentinel Node," *J Nucl Med* 34:1435–1440,1993.

van der Veen et al., "Gamma probe-guided sentinel node biopsy to select patients with melanoma for lymphadenectomy," *Br J Surg*, 81:1769–1770, 1994.

Veronesi et al., "Sentinel-node biopsy to avoid axillary dissection in breast cancer with clinically negative lymphnodes," *Lancet*, 349:1864–1867, 1997.

Villner et al. in "Multiple Sigma and PCP Receptor Ligands: Mechanisms for Neuromodulation and Neuroprotection?" Kamenka et al., eds. NPP Books, pp 341–353, 1992.

Walker et al., *Pharmacol. Reviews* 42: 355–400, 1990.

Wong et al., "Lymphatic drainage of skin to a sentinel lymph node in a feline model," *Ann Surg*, 214:637–641, 1991.

Yokota et al., "Lymph-node staining with activated carbon CH40: a new method for axillary lymph-node dissection in breast cancer," *Can J Surg*, 43:191–196, 2000.

What is claimed is:

1. A method of identifying a disease-associated sentinel lymph node in an excised tissue sample, comprising, a) administering to a subject (i) at least one fluid composition comprising of from about 0.1% carbon particles to about 6.0% carbon particles and (ii) and a standard sentinel lymph node identifier;

b) excising at least one tissue sample suspected of comprising a sentinel lymph node;

c) identifying a sentinel lymph node by a combination of the accumulation of said carbon particles and the standard sentinel lymph node identifier and d) identifying, diagnosing, staging or predicting the presence of neoplastic tissue in said lymph node based on histopathology of a subregion of the sentinel lymph node identified by carbon particle accumulation.

2. The method of claim 1, wherein the concentration of the carbon particles is between about 0.15% and about 5.0%.

3. The method of claim 1, wherein the concentration of the carbon particles is between about 0.15% and about 4.0%.

4. The method of claim 1, wherein the concentration of the carbon particles is between about 0.15% and about 3.0%.

5. The method of claim 1, wherein the concentration of the carbon particles is between about 0.15% and about 2.0%.

6. The method of claim 1, wherein the concentration of the carbon particles is between about 0.15% and about 1.0%.

7. The method of claim 1, wherein the concentration of the carbon particles is between about 0.2% to about 1.0%.

8. The method of claim 1, wherein the concentration of the carbon particles is between about 0.3% to about 1.0%.

9. The method of claim 1, wherein the concentration of the carbon particles is between about 0.4% to about 1.0%.

10. The method of claim 1, wherein the concentration of the carbon particles is between about 0.5% to about 1.0%.

11. The method of claim 1, wherein the size of the carbon particles is between about 0.1 and about 6.0 microns in diameter.

12. The method of claim 11, wherein the size of the carbon particles is between about 0.2 to about 4.0 microns in diameter.

13. The method of claim 12, wherein the size of the carbon particles is between or about 0.2 to about 2.0 microns in diameter.

14. The method of claim 13, wherein the size of the carbon particles is between about 0.2 and about 1.0 microns in diameter.

15. The method of claim 14, wherein the size of the carbon particles is between about 0.3 to about 0.8 microns in diameter.

16. The method of claim 1, wherein the size of the carbon particles is less than about 0.2 microns in diameter.

17. The method of claim 1, wherein the carbon particles comprise carbon black.

18. The method of claim 17, wherein the carbon particles comprise channel black, thermal black or furnace black.

19. The method of claim 17, wherein the carbon black is neutral.

20. The method of claim 17, wherein the carbon black is acidic.

21. The method of claim 17, wherein the carbon black is basic.

22. The method of claim 1, wherein said composition comprises a suspension of carbon particles.

23. The method of claim 1, wherein the standard sentinel lymph node identifier is a dye.

24. The method of claim 23, wherein the dye is an acid dye, a basic dye or a direct dye.

25. The method of claim 24, wherein the additional dye is a direct dye.

26. The method of claim 25, wherein the direct dye is Paper Yellow GG (CI Direct Yellow 131), Direct Scarlet 4BS (CI 29160), Congo Red (CI 22120), Violet BB (CI 27905), Direct Sky Blue 5B (CI 24400), Pentamine, Phthalocyanine Blue (CI 74180), Black G (CI 35255) or Deep Black XA (CI Direct Black 154).

27. The method of claim 23, wherein the dye is an anionic dye.

28. The method of claim 23, wherein the dye is Tartrazine (CI 19140), Quinoline Yellow (CI 47005), Eosin (CI 45380), Acid Phloxine (CI 45410), Erythrosine (CI 45430), Sunset Yellow FCF (CI 15985), Acid Violet 5B (CI 42640), Patent Blue AF (CI 42080), Brilliant Cyanine 6B (CI 42660), Acid Brilliant Blue FCF (CI 42090), Naphthalene Green VSC (CI 44025) or Acid Blue Black 10B (CI 20470).

29. The method of claim 23, wherein the dye is isosulfan blue, guajazulen blue, Patent blue V, pentamine or Direct Sky blue, or other dye which travels through the lymphatic system.

30. The method of claim 29, wherein the dye is Patent blue V.

31. The method of claim 29, wherein the dye is isosulfan blue.

32. The method of claim 31, wherein the isosulfan blue is provided as a fluid composition that comprises about 0.1% to about 3% isosulfan blue.

33. The method of claim 31, further comprising administering radiolabeled sulfur colloid said subject.

34. The method of claim 23, wherein the total dye concentration of the composition is about 0.1 to about 10 mM.

35. The method of claim 1, wherein the composition further comprises a diagnostic aid.

36. The method of claim 35, wherein the diagnostic aid is Fluorescein or Fluorescein Sodium.

37. The method of claim 1, wherein the standard sentinel lymph node identifier is a radionucleotide tracer.

38. The method of claim 37, wherein the radionucleotide tracer is technetium-labeled sulfur or albumin colloid, antimony chloride, or other colloidal radionucleotide that travels through the lymphatic system.

39. The method of claim 1, wherein the standard sentinel lymph node identifier is a receptor binding compound, an antibody or a locator.

40. The method of claim 1, wherein said administering is to the lymphatic region surrounding a neoplastic tissue.

41. The method of claim 40, wherein the neoplastic tissue is a melanoma, lung carcinoma, neuroblastoma, pheochromocytoma, colon, prostate, renal carcinoma, breast carcinoma, esophageal, gastric, pancreatic, oropharyngeal cancer or another neoplasm that metastasizes by the lymphatic channels.

42. The method of claim 41, wherein the neoplastic tissue is a melanoma.

43. The method of claim 41, wherein the neoplastic tissue is a breast carcinoma.

44. The method of claim 1, wherein the mode of administration is subcutaneous, intramuscular, intralesional, intradermal, intraperitoneal, parenteral, oral, nasal, buccal, rectal, vaginal or orthotopic.

45. The method of claim 1, wherein the time between administering and detecting the carbon particles is between about 1 minute and about 2 days.

46. The method of claim 45, wherein the time between administering and detecting the carbon particles is between about 5 minutes and about 60 minutes.

47. The method of claim 1, wherein the subject is a human.

48. The method of claim 1, wherein tissue sample is removed by a lymphadenectomy.

49. The method of claim 1, wherein a lymph node is further identified by using a hematoxylin-cosin histopathological technique, an immunohistochemical technique, spectroscopy or a cancer staging technique.

50. The method of claim 1, further comprising a microscopic examination of the lymph node.

51. The method of claim 1, further comprising, for a subject who has evidence of micrometastasis in the sentinel lymph node, performing a subsequent lymphadenectomy.

* * * * *

UNITED STATES PATENT AND TRADEMARK OFFICE
CERTIFICATE OF CORRECTION

PATENT NO. : 6,815,170 B1
DATED : November 9, 2004
INVENTOR(S) : Donald L. Morton It is certified that error appears in the above-identified patent and that said Letters Patent is hereby corrected as shown below:

Column 38,
Line 61, delete "and a" and insert -- a --.

Column 40,
Line 16, after "colloid" insert -- to --.
Line 31, delete "lvmph" and insert -- lymph --.
Line 58, delete "cosin" and insert -- eosin --.
Line 65, delete "perfonning" and insert -- performing --.

Signed and Sealed this

Third Day of May, 2005

JON W. DUDAS
*Director of the United States Patent and Trademark Office*